United States Patent
Xie et al.

(10) Patent No.: US 10,577,379 B1
(45) Date of Patent: Mar. 3, 2020

(54) FENOFIBRIC ACID SALT WITH BERBERINE OR ITS ANALOGUES, CRYSTALLINE FORMS, METHODS OF PREPARATION, AND APPLICATIONS THEREOF

(71) Applicant: Jiangxi Fushine Pharmaceutical Co., Ltd., Jingdezhen (CN)

(72) Inventors: Yongju Xie, Jingdezhen (CN); Yutao Tang, Jingdezhen (CN); Zongmin Zhao, Jingdezhen (CN); Chen Zhuo, Jingdezhen (CN); Dedong Wu, Waban, MA (US)

(73) Assignee: Jiangxi Fushine Pharmaceutical Co., Ltd., Jingdezhen (CN)

( * ) Notice: Subject to any disclaimer, the term of this patent is extended or adjusted under 35 U.S.C. 154(b) by 0 days.

(21) Appl. No.: 16/294,534

(22) Filed: Mar. 6, 2019

(30) Foreign Application Priority Data

Dec. 5, 2018 (CN) .......................... 2018 1 1478772

(51) Int. Cl.
*C07D 491/147* (2006.01)
*C07D 217/24* (2006.01)
*A61P 9/00* (2006.01)
*C07C 59/88* (2006.01)

(52) U.S. Cl.
CPC ............ *C07D 491/147* (2013.01); *A61P 9/00* (2018.01); *C07C 59/88* (2013.01); *C07D 217/24* (2013.01); *C07B 2200/13* (2013.01)

(58) Field of Classification Search
CPC ..... C07D 491/147; C07D 217/24; A61P 9/00; C07C 59/88
USPC .......................................................... 549/71
See application file for complete search history.

(56) References Cited

U.S. PATENT DOCUMENTS

| | | |
|---|---|---|
| 4,372,954 A | 2/1983 | Moreau et al. |
| 7,276,249 B2 | 10/2007 | Ryde et al. |
| 2009/0118225 A1 | 5/2009 | Krantz et al. |
| 2012/0245115 A1 | 9/2012 | Bender et al. |
| 2013/0018101 A1 | 1/2013 | Cink et al. |
| 2013/0085181 A1 | 4/2013 | Gao et al. |
| 2014/0187561 A1 | 7/2014 | Cink et al. |

FOREIGN PATENT DOCUMENTS

| | | |
|---|---|---|
| CN | 101113149 A | 1/2008 |
| CN | 101823956 A | 9/2010 |
| CN | 101935334 A | 1/2011 |
| CN | 102304103 A | 1/2012 |
| CN | 102659609 | 9/2012 |
| CN | 102702190 A | 10/2012 |
| CN | 103204850 A | 7/2013 |
| CN | 103319479 A | 9/2013 |
| CN | 104292225 A | 1/2015 |
| CN | 105168228 A | 12/2015 |
| CN | 105294676 A | 2/2016 |
| CN | 102702190 B | 4/2016 |
| CN | 105560233 A | 5/2016 |
| CN | 105566318 A | 5/2016 |
| CN | 105622602 A | 6/2016 |
| CN | 105732609 A | 7/2016 |
| CN | 105732610 * | 7/2016 |
| CN | 105801663 A | 7/2016 |
| CN | 107496397 A | 12/2017 |

OTHER PUBLICATIONS

Ling; Cardiol Res. 2013, 4, 47-55. (Year: 2013).*
Ning; Phytother. Res. 2015, 29, 668-673. (Year: 2015).*
Anderson, Neal G. "Tools for Purifying the Product: Column Chromatography, Crystallization and Reslurrying" Chapter 11 in Practical Process Research and Development: Academic Press, 2000, 223-247. (Year: 2000).*
Loewenthal, H. J. E. "Isolating and Purifying the Product" Chapter 5 in A Guide for the Perplexed Organic Experimentalist, Second Edition: Wiley & Sons, 1990, 121-153. (Year: 1990).*

* cited by examiner

Primary Examiner — Daniel R Carcanague
(74) Attorney, Agent, or Firm — McKee, Voorhees & Sease, PLC

(57) ABSTRACT

The present disclosure relates salts of fenofibric acid with berberine or its analogues, their crystalline forms, their preparation methods, and their uses, wherein the salts comprise fenofibric acid as anion and berberine or its analogues as cation. The disclosed salts of fenofibric acid with berberine or its analogues are free of unnecessary cation or anion, such as choline cation in a fenofibric acid salt with choline and chloride ion in a chloride salt of berberine or its analogs, and thus free of side effects caused by such cation or anion, including instability caused by choline and digesting system irritation caused by high acidity caused by the chloride salt of berberine analogs.

20 Claims, 7 Drawing Sheets

FENOFIBRIC ACID SALT WITH BERBERINE OR ITS ANALOGUES, CRYSTALLINE FORMS, METHODS OF PREPARATION, AND APPLICATIONS THEREOF

CROSS-REFERENCE TO RELATED APPLICATIONS

This application claims priority and is related to CN Patent Application No. CN201811478772.0, filed on Dec. 5, 2018 and entitled "FENOFIBRIC ACID SALT WITH BERBERINE OR ITS ANALOGUES, CRYSTALLINE FORMS, METHODS OF PREPARATION, AND APPLICATIONS THEREOF." The entire contents of this patent application are hereby expressly incorporated herein by reference including, without limitation, the specification, claims, and abstract, as well as any figures, tables, or drawings thereof.

FIELD OF THE INVENTION

The present disclosure relates to fenofibric acid salts, especially crystalline salts, with berberine or its analogues, which can be used in a pharmaceutical or dietary composition for the treatment or prevention of cardiovascular diseases or other conditions. The present disclosure also relates a method of preparing a crystalline salt using berberine or its analogue as cationic counter ion, particularly a crystalline fenofibric acid salt with berberine or its analogue.

BACKGROUND OF THE INVENTION

Fenofibrate, 2-[4-(4-chlorobenzoyl)phenoxy]-2-methyl-propanoic acid-1-methylethyl ester, is a lipid regulating agent. It can reduce the total cholesterol and triglyceride levels in human. Fenofibrate is usually orally administered. After oral administration, fenofibrate is metabolized in vivo to fenofibric acid. In fact, fenofibric acid is the active molecule for fenofibrate's biological functions. Thus, fenofibric acid, which demonstrates better solubility compared to fenofibrate, is a preferred chemical entity for the treatment or prevention of endogenous hyperlipidaemias, hypercholestero laemias, and hypertriglyceridaemias.

Various crystalline salts of the fenofibric acid have been investigated to optimize fenofibric acid's pharmaceutical properties. The preparation and use of some crystalline salts of fenofibric acid, including choline salt, tromethamine salt, calcium salt, diethanolamine salt, lysine salt, piperazine salt, ethanolamine salt, meglumine salt, and sodium salt have been disclosed. Among all the existing fenofibric acid salts is the choline salt of fenofibric acid.

The fenofibric acid salt with choline is the drug substance in the commercial drug product, Trilipix® (fenofibric acid capsules). However, an inherent disadvantage of using a choline salt in any pharmaceutical manufacture process or composition is the potential hazard of a choline compound, e.g. choline hydroxide or choline chloride. A choline compound can cause skin irritation, serious eye irritation, or respiratory irritation.

Another disadvantage of using a choline salt in any pharmaceutical manufacture process or composition is the instability of the choline counter ion. Through degradation, a choline molecule produces some undesired by-products, which lead to some negative consequences, such as a strong smell and color darkening for any product containing choline molecule. The instability of a choline molecule also causes any commercial pharmaceutical product to have a shorter shelf life or to require more constrained conditions for the product's handling, transportation, and storage.

Thus, it is still desirable to identify other fenofibric acid salts with better physicochemical properties, which in turn improves the manufacture process and medical use of fenofibric acid as an active therapeutic agent.

Unlike other conventional counter ions, berberine, as well as its analogues, is seldom included in a salt screening for any pharmaceutical composition. This may be due to the fact that berberine is usually commercially available as a salt, e.g. hydrochloride salt or hydrogen sulfate salt, which cannot be directly used in a traditional salt screening. In fact, the current disclosure represents the first example to use berberine or its analogues as basic counter ions to produce a new crystalline pharmaceutical salt for any pharmaceutical active agent.

Accordingly, it is an objective of the disclosure to provide solid and/or crystalline fenofibric acid salts with berberine or its analogues.

It is also an objective of this disclosure to provide pharmaceutical compositions comprising the crystalline fenofibric acid salts with berberine or its analogues disclosed herein.

It is an additional objective of this disclosure to provide a method to generate a salt using berberine or its analogs as counter ions in salts of any active pharmaceutical agent.

It is another objective of this disclosure to provide a new chemical entity having from 1:2 to 2:1, preferably 1:1 fixed ratio of fenofibric acid and berberine as co-drug for treatment of cardiovascular diseases or other diseases.

The solid and/or crystalline fenofibric acid salts with berberine or its analogues disclosed herein use natural pyridinium cations with anions of an active pharmaceutical agent in a salt and can be used alone in a pharmaceutical or dietary composition alone or with other pharmaceutical active or beneficial agent(s) for treatment or prevention of cardiovascular diseases or conditions. The crystalline fenofibric acid salts disclosed herein provide improved salt forms that uses a different counter ion, e.g., berberine or its analog, and eliminate harmful effects that are associated with the existing fenofibric acid salts, such as choline as in the commercially available Trilipix®. Thus, the crystalline salts disclosed herein provide improved chemical entities to be used in a pharmaceutical composition alone or in combination with other drug substances.

Other objects, advantages and features of the present disclosure will become apparent from the following specification taken in conjunction with the accompanying examples or drawings.

BRIEF SUMMARY OF THE INVENTION

In one aspect, provided herein is a fenofibric acid salt with berberine or its analogues. In some embodiments, the fenofibric acid salt with berberine or its analogues comprises neutralized fenofibric acid as an anion and berberine or berterine analog as a cation, wherein the berberine or berberine analog has one or more of the following structures;

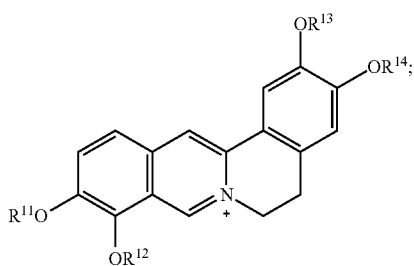

wherein $R^{11}$ and $R^{12}$ are independently H, CH$_3$, substituted or unsubstituted C$_1$-C$_3$ alkyl, or together a —CH$_2$— or substituted —CH$_2$— group; and $R^{13}$ and $R^{14}$ are independently H, CH$_3$, substituted or unsubstituted C$_1$-C$_3$ alkyl, or together a —CH$_2$— or substituted —CH$_2$— group;

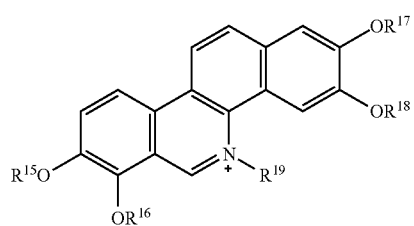

wherein $R^{15}$ and $R^{16}$ are independently H, CH$_3$, substituted or unsubstituted C$_1$-C$_3$ alkyl, or together a —CH$_2$— or substituted —CH$_2$— group; $R^{17}$ and $R^{18}$ are independently H, CH$_3$, substituted or unsubstituted C$_1$-C$_3$ alkyl, or together a —CH$_2$— or substituted —CH$_2$— group; and $R^{19}$ is H, O, CH$_3$, substituted or unsubstituted C$_1$-C$_3$ alkyl;

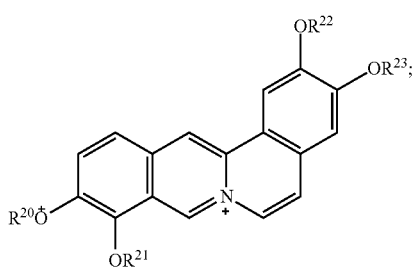

wherein $R^{20}$ and $R^{21}$ are independently H, CH$_3$, substituted or unsubstituted C$_1$-C$_3$ alkyl, or together a —CH$_2$— or substituted —CH$_2$— group; and $R^{22}$ and $R^{23}$ are independently H, CH$_3$, substituted or unsubstituted C$_1$-C$_3$ alkyl, or together a —CH$_2$— or substituted —CH$_2$— group; and

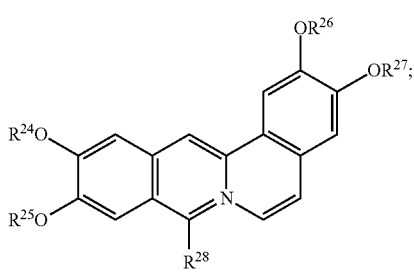

wherein $R^{24}$ and $R^{25}$ are independently H, substituted or unsubstituted C$_1$-C$_3$ alkyl, or together a —CH$_2$— or substituted —CH$_2$— group; and $R^{26}$ and $R^{27}$ are independently H, substituted or unsubstituted C$_1$-C$_3$ alkyl, or together a —CH$_2$— or substituted —CH$_2$— group; $R^{28}$ is H, substituted or unsubstituted C$_1$-C$_3$ alkyl, —OH, —OCH$_3$, —OCH$_2$CH$_3$.

As used herein, the C$_1$-C$_3$ alkyl group includes methyl, ethyl, isopropyl, propyl, or substituted group thereof.

As used herein, the substitution group as in the substituted C$_1$-C$_3$ alkyl or —CH$_2$— group includes, but are not limited to, C$_1$-C$_3$ alkyl, alkenyl, halogen (Cl, F, Br, etc.), aryl, —NO$_2$, amine, alcohol, or ether group.

In another aspect, the salt disclosed herein is a fenofibric acid salt with berberine or its analogues, is in crystalline form, and is characterized by an XRPD pattern comprising one or more peaks expressed as 2θ±0.2° of about 6.1°, about 7.8°, about 12.2°, about 15.6°, about 17.3°, about 18.3°, about 18.6°, about 19.6°, about 20.4°, and about 25.4°.

In another aspect, the disclosed herein is a method to prepare the crystalline Form A of fenofibric salt with berberine or its analogues, the method comprises suspending a berberine, its analog, or salt thereof in an alcohol solvent (including, but is not limited to MeOH or ethanol) to obtain a suspension or solution; adding a base (including, but is not limited to NaOH or potassium hydroxide) and fenofibric acid or its salt; stirring the suspension in a temperature of about 50-70° C. to obtain an orange solution; cooling the solution to room temperature to precipitate yellowish crystalline Form A of fenofibric salt with berberine or its analogues; filtering, washing, and/or dry the resulted solid to obtain the crystalline Form A.

In another aspect, the salt disclosed herein is a crystalline form of fenofibric salt with berberine or its analogues, characterized by its crystalline group (P-1) and/or dimensions (a=7.0792(4) Å, b=14.6702(7)Å, c=16.3544(8) Å, α=83.881(2)°, β=83.306(2)°, γ=87.352(2)°, V=1676.29(15) Å$^3$).

In another aspect, the salt disclosed herein is a fenofibric acid salt with berberine or its analogues, is in crystalline form; e.g. crystalline Form B of fenofibric acid salt with berberine or its analogues, and is characterized by an XRPD pattern comprising one or more peaks expressed as 2θ±0.2° of about 6.2°, about 8.0°, about 12.4°, about 12.9°, about 15.9°, about 17.3°, about 18.7°, about 19.8°, about 20.9°, and about 25.5°.

In another aspect, disclosed herein is a method to prepare the crystalline Form B of fenofibric acid salt with berberine or its analogues, wherein the method comprises suspending a fenofibric acid salt with berberine in any solid from (including, but is limited to Form A, amorphous, or other crystalline form) in water to obtain a suspension or solution; stirring the suspension in room temperature for about 12-48 hours; filtering, and/or air dry the resulted solid to obtain the crystalline Form B.

In another aspect, the salt disclosed herein is a fenofibric acid salt with berberine, is in crystalline form; e.g. crystalline Form C of fenofibric acid salt with berberine, and is characterized by an XRPD pattern comprising one or more peaks expressed as 2θ±0.2° of about 6.0°, about 7.7°, about 12.1°, about 15.5°, about 18.2°, about 18.5°, about 19.5°, about 20.3°, about 25.7°, and about 32.3°.

In another aspect, disclosed herein is a method to prepare the crystalline Form C of fenofibric acid salt with berberine or its analogues, wherein the method comprises suspending fenofibric acid or its salt in water and adding NaOH or its solution into the fenofibric acid solution to obtain a clear fenofibric and NaOH solution; dissolving berberine or its salt into water to obtain an orange solution; adding the clear solution slowly into the orange solution to obtain a precipitated yellow solid and then to generate a double-layer solution; adding ethanol into the double-layer solution; stirring the double-layer solution for about 12-18 hours; and then filtering, washing, and/or air-drying the collected solid to obtain the crystalline Form C of fenofibric acid salt with berberine or its analogues.

In another aspect, the salt disclosed herein is a fenofibric acid salt with berberine or its analogues, is in crystalline form; e.g. crystalline Form D of fenofibric acid salt with berberine, and is characterized by an XRPD pattern comprising one or more peaks expressed as 2θ±0.2° of about 5.5°, about 6.9°, about 7.8°, about 9.7°, about 15.7°, about 15.9°, about 17.0°, about 19.2°, about 20.0°, and about 21.3°.

In another aspect, disclosed herein is a method to prepare the crystalline Form D of fenofibric acid salt with berberine or its analogues, wherein the method comprises dissolving fenofibric acid or its salt in a NaOH solution to obtain a clear fenofibric and NaOH solution; suspending berberine or its salt into the clear solution to obtain a suspension; adding MeOH into the suspension, heating the suspension to about 50-70° C. to obtain a deep orange solution, filtering and condense the orange solution under room temperature to precipitate a yellow solid to obtain a second suspension solution; adding more water to the second suspension solution and stirring the second solution for about 12-48 hours; filtering and wash with water the resulted solid from the second suspension to obtain the crystalline Form D of fenofibric acid salt with berberine. In some embodiments, the method further comprises drying the resulted solid in vacuum at a temperature of about 35-45° C.

In another aspect, disclosed herein is another method to prepare the crystalline Form D of fenofibric acid salt with berberine or its analogues; wherein the method comprises heating another crystalline form of fenofibric acid salt with berberine, such as Form A, Form B, Form C, or other crystalline form of fenofibric acid salt with berberine or its analogues, or dissolving the another crystalline form of fenofibric acid salt with berberine into EtOAc or other solvent.

In another aspect, the salt disclosed herein is a fenofibric acid salt with berberine or its analogues, is in crystalline form; e.g. crystalline Form E of fenofibric acid salt with berberine or its analogues, and is characterized by an XRPD pattern comprising one or more peaks expressed as 2θ±0.2° of about 7.9°, about 13.1°, about 15.8°, about 16.9°, about 17.7°, about 20.7°, about 26.1°, about 26.4°, about 27.0°, and about 27.6°.

In another aspect, disclosed herein is another method to prepare the crystalline Form E of fenofibric acid salt with berberine or its analogues; wherein the method comprises suspending fenofibric acid or its salt in water and adding NaOH or its solution into the fenofibric acid solution to obtain a clear fenofibric and NaOH solution; dissolving berberine or its salt into hot water to obtain an orange solution; adding the clear solution slowly into the hot orange solution to obtain a precipitated yellow solid; cooling down the mixed solution and solid within to room temperature and stirring it for about 40-100 minutes to generate a double-layer solution; adding ethanol into the double-layer solution to precipitate a yellow solid; keeping stirring the double-layer solution for about 10-48 hours; and then filtering, washing, and/or air-drying the resulted solid to obtain the crystalline Form E of fenofibric acid salt with berberine.

In another aspect, the salt disclosed herein is a fenofibric acid salt with berberine or its analogues, is in crystalline form; e.g. crystalline Form F of fenofibric acid salt with berberine, and is characterized by an XRPD pattern comprising one or more peaks expressed as 2θ±0.2° of about 5.3°, about 5.6°, about 6.6°, about 8.4°, about 14.0°, about 17.6°, about 19.2°, about 23.4°, about 25.1°, and about 25.7°.

In another aspect, disclosed herein is another method to prepare the crystalline Form F of fenofibric acid salt with berberine or its analogues; wherein the method comprises heating Form E of fenofibric acid salt with berberine to a temperature of about 90-110° C. for about 40-100 minutes to obtain Form F of fenofibric acid salt with berberine.

In another aspect, the salt disclosed herein is a fenofibric acid salt with berberine, is in crystalline form; e.g. crystalline Form G of fenofibric acid salt with berberine, and is characterized by an XRPD pattern comprising one or more peaks expressed as 2θ±0.2° of about 6.1°, about 7.8°, about 12.1°, about 12.3°, about 12.9°, about 13.8°, about 15.8°, about 17.3°, about 19.7°, and about 20.8°.

In another aspect, disclosed herein is another method to prepare the crystalline Form G of fenofibric acid salt with berberine or its analogues; wherein the method comprises dissolving Form E of fenofibric acid salt with berberine in isopropanol and water (volume ratio of from about 1:2 to about 2:1) to obtain a clear yellow solution; vaporizing water and isopropanol from the clear solution to obtain a powder of Form G of fenofibric acid salt with berberine.

In another aspect, the salt disclosed herein is a fenofibric acid salt with berberine or its analogues, is in crystalline form; e.g. crystalline Form H of fenofibric acid salt with berberine, and is characterized by an XRPD pattern comprising one or more peaks expressed as 2θ±0.2° of about 5.5°, about 6.5°, about 8.0°, about 8.3°, about 10.9°, about 12.9°, about 14.0°, about 17.5°, about 17.9°, about 22.0°, and about 23.2°.

In another aspect, disclosed herein is another method to prepare the crystalline Form H of fenofibric acid salt with berberine; wherein the method comprises suspending Form A of fenofibric acid salt with berberine or its analogues into EtOAc or its solution to obtain a solution, stirring the solution under room temperature for about 2-4 days; and filtering out the resulted solid to obtain Form H of fenofibric acid salt with berberine or its analogues.

In yet another aspect, disclosed herein is a method of therapeutic or prophylactic treatment of a subject against cardiovascular diseases or other conditions, the method comprises administering a therapeutically effective amount of a fenofibric acid salt with berberine or its analog disclosed herein to a subject in need of cardiovascular diseases or other condition care.

In another aspect, disclosed herein is a method of therapeutic or prophylactic treatment of a subject against cardiovascular diseases or other conditions, the method comprises administering a therapeutically effective amount of one or more of the disclosed crystalline fenofibric acid salts with berberine or its analogs, e.g. Form A-Form H disclosed herein, to a subject in need of cardiovascular diseases or other condition care.

In another aspect, disclosed herein is a method for preparing a salt disclosed herein, wherein the method comprises mixing berberine hydroxide or a mixture of berberine salt with a hydroxide with fenofibric acid or salt thereof.

In yet another aspect, disclosed herein is a method for preparing a berberine or its analog salt of an active pharmaceutical agent, wherein the method comprises mixing berberine hydroxide or a mixture of berberine salt with a hydroxide with an active pharmaceutical agent, wherein the active pharmaceutical agent is capable to form an anion and form a salt with berberine or its analog.

The fenofibric acid salts with berberine or its analogs disclosed herein eliminate undesired counter ions, specifically, choline cation for a fenofibric salt and/or chloride anion for a berberine salt, from a commercially available drug, so reduce some side effects caused by these two counter ions, including gastrointestinal irritation due to the high acidity of berberine hydrochloride salt.

Furthermore, the fenofibric acid salts with berberine or its analogs disclosed herein are new chemical entities, which demonstrate acceptable pharmaceutical property to treat cardiovascular diseases or conditions.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION OF THE INVENTION

Figure 1:
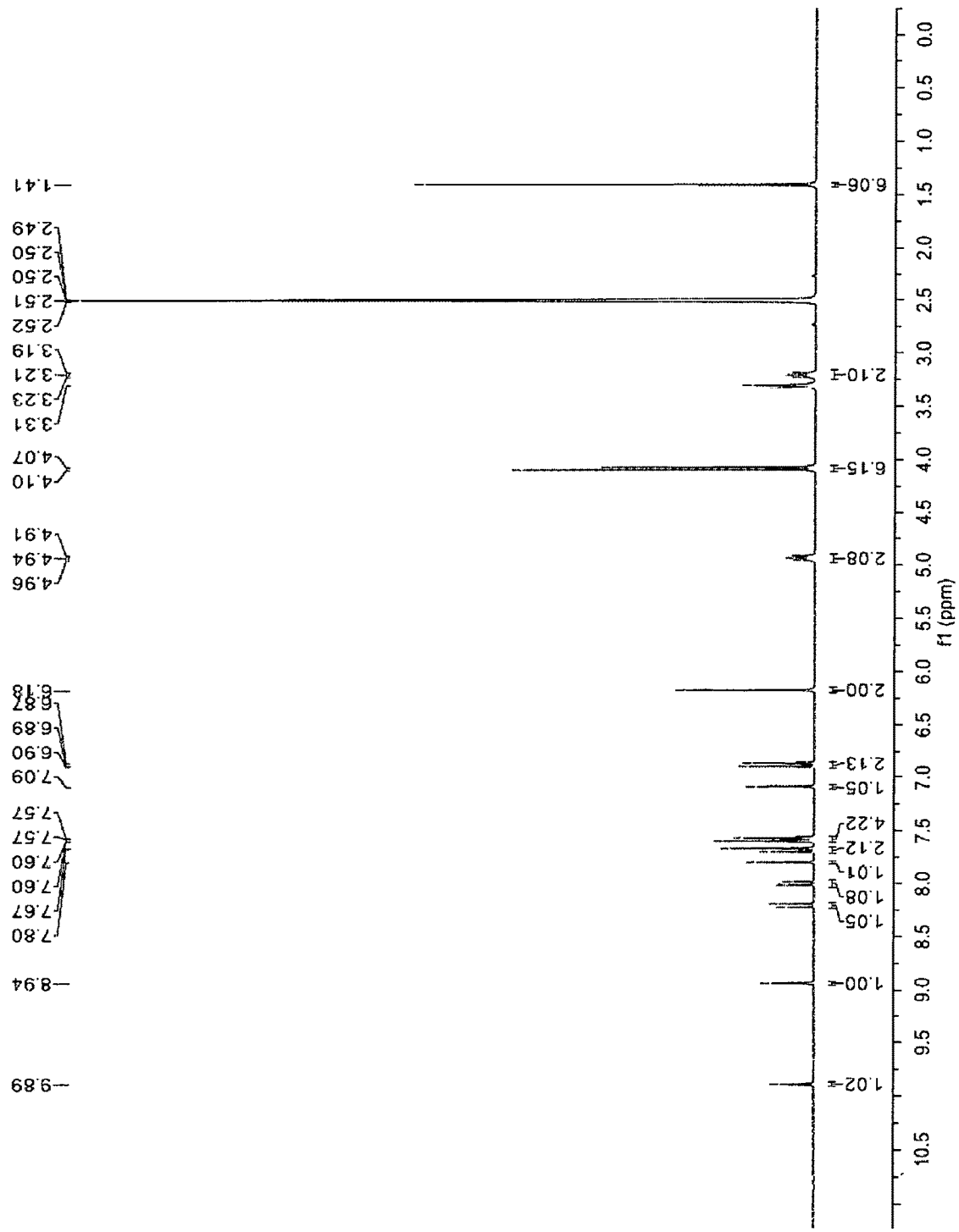
FIG. 1 shows the $^1$H NMR spectrum of a fenofibric acid salt with berberine (Form A salt).

The present disclosure relates to solid and/or crystalline fenofibric acid salts with berberine or its analogs, pharmaceutical or dietary compositions thereof, methods of preparation thereof, and methods of using berberine or its analog for salt screening of an acidic active pharmaceutical agent. Using berberine or its analog as counter ion for a crystalline salt can not only improve physicochemical properties of the active agent, specially fenofibric acid, but also enhance or expand therapeutic effects of the active anion agent because berberine or its analogues also possess some therapeutic effect of its own.

The embodiments of this disclosure are not limited to particular compositions and methods, which can vary and are understood by skilled artisans. It is further to be understood that all terminology used herein is for the purpose of describing particular embodiments only and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this disclosure are presented in a range format. The description in range format is merely for convenience and brevity and should not be construed as an inflexible limitation on the scope of the disclosure. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present disclosure may be more readily understood, certain terms are first defined. Unless defined otherwise, all technical and scientific terms used herein have the same meaning as commonly understood by one of ordinary skill in the art to which embodiments of the disclosure pertain. Many methods and materials similar, modified, or equivalent to those described herein can be used in the practice of the embodiments of the present disclosure without undue experimentation, the preferred materials and methods are described herein. In describing and claiming the embodiments of the present disclosure, the following terminology will be used in accordance with the definitions set out below.

The term "about," as used herein, refers to variation in the numerical quantity that can occur, for example, through typical measuring and liquid handling procedures used for making concentrates or use solutions in the real world; through error in these procedures; through differences in the manufacture, source, or purity of the ingredients used to make the compositions or carry out the methods; and the like. The term "about" also encompasses amounts that differ due to novel equilibrium conditions for a composition resulting from a particular initial mixture. Whether or not modified by the term "about", the claims include equivalents to the quantities.

As used herein, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to carbon(s) or hydrogen(s) atom replaced by one or more bonds, including double or triple bonds, to a heteroatom. Thus, a substituted group is substituted with one or more substituents, unless otherwise specified. A substituted group can be substituted with 1, 2, 3, 4, 5, or 6 substituents.

Substituted ring groups include rings and ring systems in which a bond to a hydrogen atom is replaced with a bond to a carbon atom. Therefore, substituted cycloalkyl, aryl, heterocyclyl, and heteroaryl groups may also be substituted with substituted or unsubstituted alkyl, alkenyl, and alkynyl groups are defined herein.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Alkenyl groups or alkenes are straight chain, branched, or cyclic alkyl groups having two to about 30 carbon atoms, and further including at least one double bond. In some embodiments, an alkenyl group has from 2 to about 30 carbon atoms, or typically, from 2 to 10 carbon atoms. Alkenyl groups may be substituted or unsubstituted. For a double bond in an alkenyl group, the configuration for the double bond can be a trans or cis configuration. Alkenyl groups may be substituted similarly to alkyl groups.

Alkynyl groups are straight chain, branched, or cyclic alkyl groups having two to about 30 carbon atoms, and further including at least one triple bond. In some embodiments, an alkynyl group has from 2 to about 30 carbon atoms, or typically, from 2 to 10 carbon atoms. Alkynyl groups may be substituted or unsubstituted. Alkynyl groups may be substituted similarly to alkyl or alkenyl groups.

As used herein, the terms "alkylene", cycloalkylene", "alkynylides", and "alkenylene", alone or as part of another substituent, refer to a divalent radical derived from an alkyl, cycloalkyl, or alkenyl group, respectively, as exemplified by —$CH_2CH_2CH_2$—. For alkylene, cycloalkylene, alkynylene, and alkenylene groups, no orientation of the linking group is implied.

The term "ester" as used herein refers to —$R^{30}COOR^{31}$ group. $R^{30}$ is absent, a substituted or unsubstituted alkylene, cycloalkylene, alkenylene, alkynylene, arylene, aralkylene, heterocyclylalkylene, or heterocyclylene group as defined herein. $R^{31}$ is a substituted or unsubstituted alkyl, cycloalkyl, alkenyl, alkynyl, aryl, aralkyl, heterocyclylalkyl, or heterocyclyl group as defined herein.

The term "amine" (or "amino") as used herein refers to —$R^{32}NR^{33}R^{34}$ groups. $R^{32}$ is absent, a substituted or unsubstituted alkylene, cycloalkylene, alkenylene, alkynylene, arylene, aralkylene, heterocyclylalkylene, or heterocyclylene group as defined herein. $R^{33}$ and $R^{34}$ are independently hydrogen, or a substituted or unsubstituted alkyl, cycloalkyl, alkenyl, alkynyl, aryl, aralkyl, heterocyclylalkyl, or heterocyclyl group as defined herein.

The term "amine" as used herein also refers to an independent compound. When an amine is a compound, it can be represented by a formula of $R^{32'}NR^{33'}R^{34'}$ groups, wherein $R^{32'}$, $R^{33'}$, and $R^{34'}$ are independently hydrogen, or a substituted or unsubstituted alkyl, cycloalkyl, alkenyl, alkynyl, aryl, aralkyl, heterocyclylalkyl, or heterocyclyl group as defined herein.

The term "alcohol" as used herein refers to —$R^{35}OH$ groups. $R^{35}$ is absent, a substituted or unsubstituted alkylene, cycloalkylene, alkenylene, alkynylene, arylene, aralkylene, heterocyclylalkylene, or heterocyclylene group as defined herein.

The term "carboxylic acid" as used herein refers to —$R^{36}COOH$ groups. $R^{36}$ is absent, a substituted or unsubstituted alkylene, cycloalkylene, alkenylene, alkynylene, arylene, aralkylene, heterocyclylalkylene, or heterocyclylene group as defined herein.

The term "ether" as used herein refers to —$R^{37}OR^{38}$ groups. $R^{37}$ is absent, a substituted or unsubstituted alkylene, cycloalkylene, alkenylene, alkynylene, arylene, aralkylene, heterocyclylalkylene, or heterocyclylene group as defined herein. $R^{38}$ is a substituted or unsubstituted alkyl, cycloalkyl, alkenyl, alkynyl, aryl, aralkyl, heterocyclylalkyl, or heterocyclyl group as defined herein.

The term "solvent" as used herein refers to any inorganic or organic solvent. Certain solvents can be a part of the crystalline salts disclosed herein. Solvents are useful in the disclosed method or article, product, or composition as reaction solvent or carrier solvent. Suitable solvents include, but are not limited to, lower alkyl alcohols, aliphatic and aromatic hydrocarbons, dialkyl ethers, dialkyl ketones, alkyl acetates, acetonitrile, chlorinated alkanes, dimethyl sulfoxide (DMSO), dimethylformamide (DMF), and aqueous solvents, Examples of solvents include, but are not limited to, methanol, ethanol, propanol, isopropanol and butanol, isobutanol, ethyl acetate, iso-propyl acetate, n-heptane, diethyl ether, tert-butyl methyl ether, acetone, dichloromethane, or water, The solvent used herein can be of a single solvent or a mixture of many different solvents.

Fenofibric Acid and Berberine and its Analogs

The solid and/or crystalline salts disclosed herein are solid and/or crystalline fenofibric acid salt with berberine or its analogs. Fenofibric acid has the following structure.

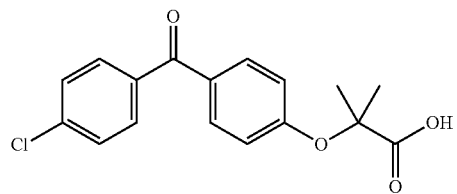 [SMILES: CC(C)(Oc1ccc(C(=O)c2ccc(Cl)cc2)cc1)C(=O)O]

A neutralized fenofibric acid, as referred herein, is an anion having a formula of

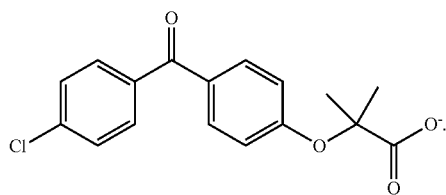

Berberine is a molecule (cation) with the following structure.

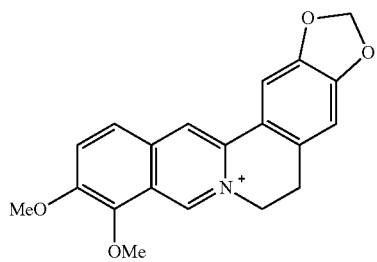 [SMILES: COc1ccc2cc3[n+](cc2c1OC)CCc1cc2c(cc1-3)OCO2]

Berberine is an isoquinoline plant alkaloid endowed with several pharmacological activities, including anti-microbial, glucose-lowering, cholesterol-lowering, anti-tumoral, and immunomodulatory properties. Berberine has been used in China as a traditional medicine and as a dietary supplement for various health benefits. Berberine has been proved to be safe for human consumption.

Notably, berberine is regarded as a novel cholesterol-lowering medicine working through a unique mechanism distinct from statins. Thus, the fenofibric acid salts disclosed herein represent a novel lipid regulating co-drug agent to replace other fenofibric salts, fenofibric salt based pharmaceutical composition/drug, or the combination use of statins and fenofibrates. Furthermore, berberine is also found to be effective for diabetes mellitus treatment, representing a promising drug candidate as an alternative of metformin, the first-line medication for the treatment of type 2 diabetes. Therefore, the fenofibric acid salts with berberine or its analogs disclosed herein provide combined benefits from both fenofibric acid salt and berberine salt for patients with cardiovascular diseases or other conditions.

Other quaternary pyridinium analogues of berberine, e.g. copisine, jatrorrhizine, palmarine, berberubine, thalifendine, demethyleneberberine, coralyne, sanguinarine, et al., demonstrated similar therapeutic effects.

A berberine analog, as used herein, refers to a molecule with the one of the following generic structures,

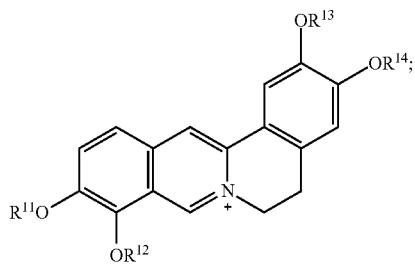

wherein $R^{11}$ and $R^{12}$ are independently H, $CH_3$, substituted or unsubstituted $C_1$-$C_3$ alkyl, or together a —$CH_2$— or substituted —$CH_2$— group; and $R^{13}$ and $R^{14}$ are independently H, $CH_3$, substituted or unsubstituted $C_1$-$C_3$ alkyl, or together a —$CH_2$— or substituted —$CH_2$— group;

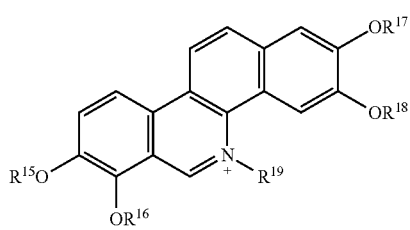

wherein $R^{15}$ and $R^{16}$ are independently H, $CH_3$, substituted or unsubstituted $C_1$-$C_3$ alkyl, or together a —$CH_2$— or substituted —$CH_2$— group; $R^{17}$ and $R^{18}$ are independently H, $CH_3$, substituted or unsubstituted $C_1$-$C_3$ alkyl, or together a —$CH_2$— or substituted —$CH_2$— group; and $R^{19}$ is H, O, $CH_3$, substituted, or unsubstituted $C_1$-$C_3$ alkyl;

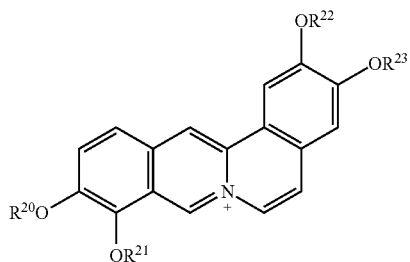

wherein $R^{20}$ and $R^{21}$ are independently H, $CH_3$, substituted or unsubstituted $C_1$-$C_3$ alkyl, or together a —$CH_2$— or substituted —$CH_2$— group; and $R^{22}$ and $R^{23}$ are independently H, $CH_3$, substituted or unsubstituted $C_1$-$C_3$ alkyl, or together a —$CH_2$— or substituted —$CH_2$— group; and

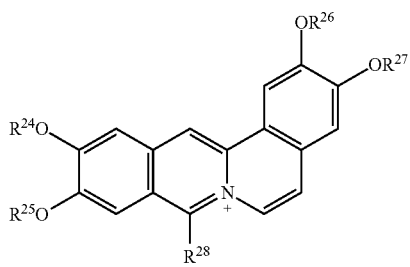

wherein $R^{24}$ and $R^{25}$ are independently H, substituted or unsubstituted $C_1$-$C_3$ alkyl, or together a —$CH_2$— or substituted —$CH_2$— group; and $R^{26}$ and $R^{27}$ are independently H, substituted or unsubstituted $C_1$-$C_3$ alkyl, or together a —$CH_2$— or substituted —$CH_2$— group; $R^{28}$ is H, substituted or unsubstituted $C_1$-$C_3$ alkyl, —OH, —$OCH_3$, or —$OCH_2CH_3$.

The substitution group for $C_1$-$C_3$ alkyl group of $R^{11}$-$R^{28}$ include, but not limited to, halogen, —OH, —CN, or —$NH_2$.

A specific berberine analog can be, but is not limited to, one of the followings:

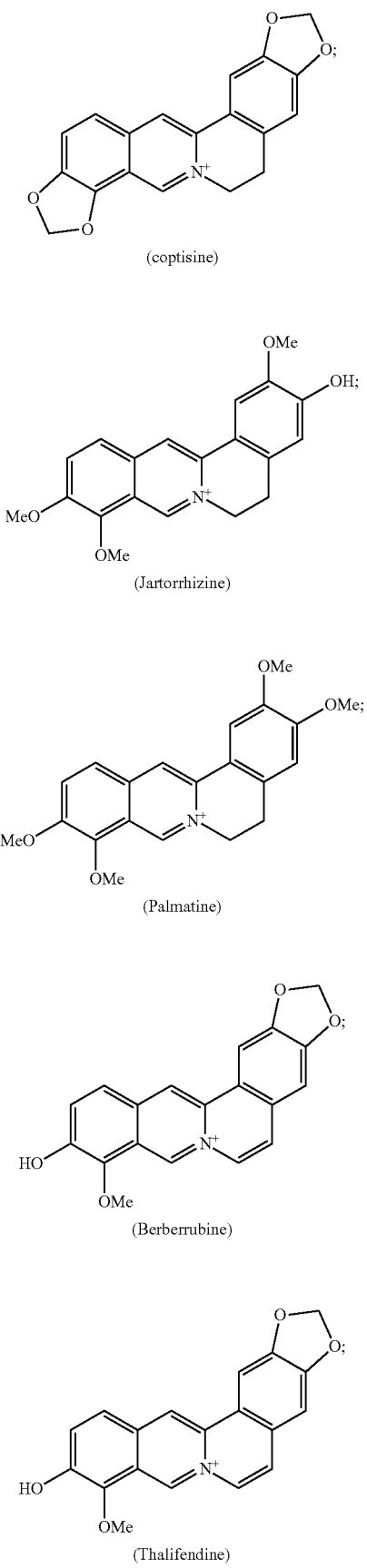 [SMILES: c1c2c(cc3c1OCO3)-c1cc3ccc4c(c3c[n+]1CC2)OCO4 ; COc1cc2c(cc1O)CC[n+]1cc3c(OC)c(OC)ccc3cc1-2 ; COc1cc2c(cc1OC)-c1cc3ccc(OC)c(OC)c3c[n+]1CC2 ; COc1c(O)ccc2cc3c4cc5c(cc4cc[n+]3cc12)OCO5 ; COc1c(O)ccc2cc3c4cc5c(cc4cc[n+]3cc12)OCO5]

-continued

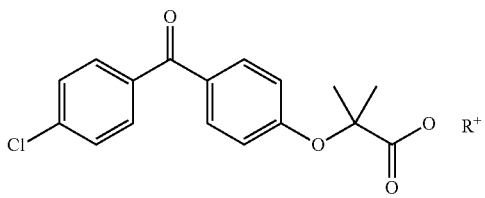

Fenofibric Acid Salts with Berberine or Berberine Analog

A fenofibric acid salt with berberine or its analog, as used herein, is referred to a solid salt having a formula of wherein $R^+$ is berberine, a berberine analog, or a mixture thereof or $R^+$ is from berberine, a berberine analog, or a mixture thereof. A fenofibric acid salt with berberine disclosed herein has berberine or its analog as the salt's cation and neutralized fenofibric acid as the salt's anion.

In some embodiments, a fenofibric acid salt with berberine or its analog as disclosed herein comprises berberine or its analog as about 99.9% or more in molar percentage of the counter cations for the neutralized fenofibric acid. In some other embodiments, a fenofibric acid salt with berberine or its analog as disclosed herein comprises berberine or its analog as about 99.5% or more, about 95.5% or more, about 90% or more, about 85% or more, about 80% or more, about 75% or more, about 70% or more, about 65% or more, about 60% or more, about 55% or more, about 50% or more, or about 40% or more in molar percentage of its cations for the neutralized fenofibric acid.

When the counter ion for the neutralized fenofebric acid is not 100% berberine or its analog, any other common cation or known counter ions for fenofebric acid can be used in a fenofibric acid salt with berberine or its analog as disclosed herein.

A crystalline fenofibric acid salt with berberine or its analog as disclosed herein is a solid crystalline fenofibric acid salt as indicated by powder X-ray pattern or solid NMR. A crystalline solid can be single crystal solid or a mixture of more than one types or forms of crystalline solids.

Method of Preparing Fenofibric Acid Salts with Berberine or Berberine Analogs

An exemplary reaction scheme to prepare fenofibric acid salt with berberine is shown below.

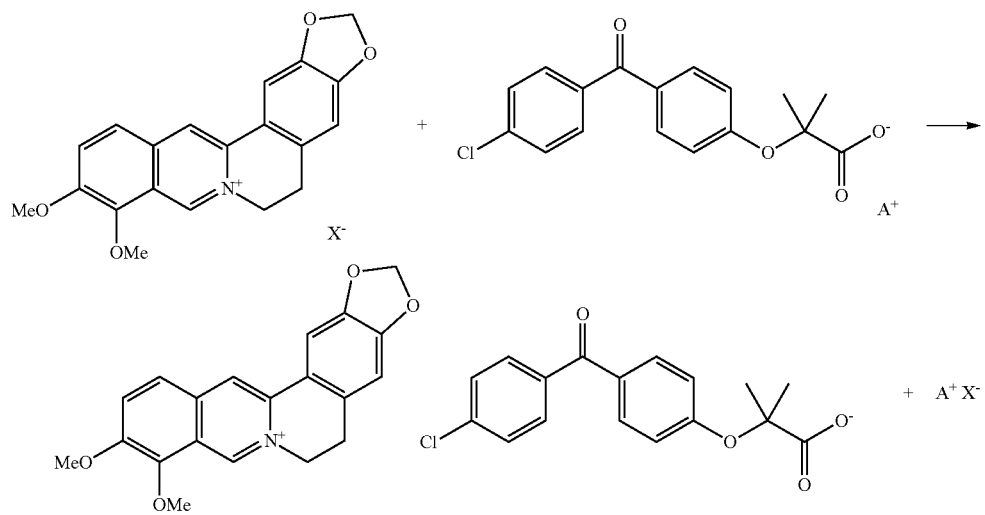

wherein $X^-$ is $OH^-$, $Cl^-$, $Br^-$, $I^-$, $HSO_4^-$, $SO_4^{2-}$, or other inorganic or organic counter ion; and $A^+=H^+$, $Na^+$, $K^+$, or other inorganic or organic counter ion.

A fenofibric acid salt with berberine as disclosed herein can be prepared by various methods. Some specific methods for preparing a fenofibric acid salt with berberine as disclosed herein include, but are not limited to, (a) the reaction of the fenofibric acid and the berberine and its analogues in a hydroxide form; (b) if a hydroxide form of berberine and its analogues is not the starting material, an inorganic salt of fenofibric acid, such as sodium salt or potassium salt, can be prepared and used for the salt preparation with berberine or its analog. For example, a fenofibric acid salt with berberine as disclosed herein can be produced by the reaction of berberine chloride or berberine hemisulfate and sodium fenofibrate, which is prepared from fenofibric acid and sodium hydroxide, followed by isolation of the desired fenofibric salt from the inorganic by-product, e.g. NaCl or KCl; or (c) fenofibric acid can be mixed directly with commercial available raw material of berberine or its analogues in chloride or other salt form, then titrate the mixture with sodium hydroxide, potassium hydroxide or other bases, followed by separation of the desired fenofibric salt from inorganic by-product, e.g. NaCl and KCl. Depending on commercial forms of the raw materials of fenofibric acid and berberine (or its analogues), large-scale manufacture can be achieved by one of these methods disclosed herein for commercial product development.

In the disclosed methods to prepare a crystalline form of fenofibric acid salt with berberine, a ratio between fenofibric acid and berberine or its analog is from about 1:2 to about 2:1, preferably about 1:1.

Crystallization and Solid Forms of Fenofibric Acid Salt with Berberine or its Analog An optimal solid form of fenofibric acid salt with berberine or its analog can be developed to possess suitable physicochemical properties for its pharmaceutical or dietary composition. The optimal form also improves in vivo delivery in human of both fenofibric acid and berberine.

The term "solid form", "solid", or related terms, as used herein, refer to a physical form that is not predominantly in a liquid or a gaseous state. A solid form may be crystalline, amorphous, or a mixture thereof. A "salt", as used herein, refers to a solid comprising both anions and cations in equal molar amount. A salt can be a "single-component" solid. A salt can also be a "multiple-component" solid comprising one or more additional species, such as nonionic molecules, cocrystal molecules, and/or solvent molecules. For example, a crystalline multiple-component salt further comprises one or more non-covalently bonded species at regular positions in its crystal lattice.

The term "crystalline", "crystalline solid", "crystal solid", "crystal form", or related terms, as used herein, refer to any solid substance, material, compound, a mixture of compounds, or product exhibiting three-dimensional order, which is in contrast to an amorphous solid substance, giving a distinctive PXRD pattern or solid NMR spectrum with sharply defined peaks.

The term "solvate" describes a molecular complex comprising a salt, compound, drug substance, or mixture thereof and a stoichiometric or non-stoichiometric amount of one or more solvent molecules (e.g., ethanol). When the solvent is tightly bound to the salt, compound, or drug substance, the resulting complex will have a well-defined stoichiometry that is independent of humidity. When, however, the solvent is weakly bound, as in channel solvates and hygroscopic compounds, the solvent content will be dependent on humidity and drying conditions. In such cases, the complex will often be non-stoichiometric.

The term "hydrate" describes a solvate comprising the drug substance and a stoichiometric or non-stoichiometric amount of water.

As used herein, "non-hydroscopic" means having little or no tendency to absorb moisture or water. As used herein, "anhydrous" means having little, no water, or free of water.

The term "powder X-ray diffraction pattern", "PXRD pattern", or "powder X-ray diffraction diagram" refers to the experimentally observed diffractogram or parameters derived therefrom. Powder X-ray diffraction patterns are characterized by peak position (abscissa) and peak intensities (ordinate).

The term "2 theta value" or "2θ" refers to the peak position in degrees based on the experimental setup of the X-ray diffraction experiment and is a common abscissa unit in diffraction patterns. The experimental setup requires that if a reflection is diffracted when the incoming beam forms an angle theta (θ) with a certain lattice plane, the reflected beam is recorded at an angle 2 theta (2θ). The reference herein to specific 2θ values for a specific solid form is intended to mean the 2θ values (in degrees) as measured using the X-ray diffraction experimental conditions as described herein.

A crystalline solid can be single component or multiple components solid. Crystalline solid includes, but is not limited to, a polymorph, single crystal, solvate (including hydrates), or mixture thereof. In some embodiments, a crystalline solid is crystalline as determined, e.g., by XRPD, solid NMR, Raman spectroscopy, polarized light microscopy (PLM), and/or moisture absorption analysis. In some embodiments, a crystalline solid comprises about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, about 100%, or any value there between of crystalline material. In some embodiments, a crystalline solid of a substance may be substantially free of or free of an amorphous form. In some embodiments, a crystalline solid of a substance may be "physically pure," e.g., contains less than about 1%, about 2%, about 3%, about 4%, about 5%, about 6%, about 7%, about 8%, about 9%, about 10%, about 15%, about 20%, about 25%, about 30%, about 35%, or about 40% of other crystal forms or amorphous forms on a weight basis. In some embodiments, a crystal form of a substance may be "chemically pure," e.g. contains less than about 1%, about 2%, about 3%, about 4%, about 5%, about 6%, about 7%, about 8%, about 9%, about 10%, about 15%, about 20%, about 25%, about 30%, about 35%, or about 40% of other chemical substances on a weight basis.

The terms "polymorphs," "polymorphic forms", or related terms refer to a crystalline solid comprising two or more crystal forms of the same molecule, mixtures of molecules, salt, or combination thereof.

The term "neat form" refer to a solid form of a substance which contains only acidic counter ion and the basic counter ion of the salt.

The terms "polymorphs of solvates" refers to the existence of more than one crystal forms for a particular solvate composition. Similarly, "polymorphs of hydrates" refers to the existence of more than one crystal forms for a particular hydrate composition. The term "desolvated solvate" refers to a crystal form of a substance which may be prepared by removing the solvent from a solvate.

The terms "co-crystal" and "co-crystallized" refer to a solid form of a substance which contains the salt and cocrystal formers. The cocrystal formers, which is a solid form at the ambient temperature, include acids, bases, neutral compounds, or mixture thereof. "Polymorphs of cocrystals" refers to the existence of more than one crystal forms for a particular cocrystal composition. Similarly, "solvate or hydrate of co-crystal" refers crystal solvate or hydrate form for a particular co-crystal composition.

The term "amorphous," "amorphous form," or related terms refer to a substance, component, or product that is not crystalline as determined by X-ray diffraction, solid NMR, or other analytical techniques as known by one skilled in the art. In particular, the term "amorphous form" describes a disordered solid form, e.g. a solid form lacking long range crystalline order.

Solid forms comprising the crystalline salt can be prepared by the methods described herein, including the methods described in the Examples below, or by techniques including, but not limited to, heating, cooling, freeze drying, lyophilization, spray drying, quench cooling the melt, rapid solvent evaporation, slow solvent evaporation, solvent recrystallization, antisolvent addition, slurry recrystallization, crystallization from the melt, desolvation, recrystallization in confined spaces such as, e.g., in nanopores or capillaries, recrystallization on surfaces or templates such as, e.g., on polymers, recrystallization in the presence of additives, desolvation, dehydration, rapid cooling, slow cooling, exposure to solvent and/or water, drying, including, e.g., vacuum drying, vapor diffusion, sublimation, grinding (including, e.g., cryo-grinding and solvent-drop grinding), microwave-induced precipitation, sonication-induced precipitation, laser-induced precipitation and precipitation from a supercritical fluid. Unless otherwise specified, methods involving solvents described herein contemplate the use of any suitable common laboratory solvent, as known in the art. The particle size of resulting solid forms, which can vary, (e.g., from nanometer dimensions to millimeter dimensions), can be controlled, e.g.: by varying crystallization conditions (such as, e.g., the rate of crystallization and/or the crystallization solvent system); by altering spray drying operating parameters (including, e.g., feed solution concentration); and/or equipment design or by particle-size reduction techniques (e.g., grinding, milling, micronizing or sonication).

Crystallization temperatures and crystallization times depend upon the salt that is to be crystallized, the concentration of that salt in solution, and the solvent system which is used.

Crystallization may also be initiated and/or effected by way of standard techniques, for example with or without seeding with crystals of the appropriate crystalline salt of this disclosure.

Different crystalline solid of the same compound often possess different solid-state properties such as melting point, solubility, dissolution rate, hygroscopicity, powder flow, mechanical properties, chemical stability and physical stability. These solid-state properties may offer advantages in filtration, drying, and dosage form manufacturing unit operations. Thus, once different crystalline solid forms of the same compound have been identified, the optimum crystalline solid under any given set of processing and manufacturing conditions may be determined as well as the different solid-state properties of each crystalline solid.

X-ray Powder diffraction (XRPD) technique is regarded as the "golden tool" for identifying, analyzing, and/or characterizing crystalline forms. It also provides a finger print for each crystalline form with unique molecular conformation and molecular packing in its crystal lattice. The crystalline salts disclosed herein were characterized by X-ray powder diffraction technique and found to have unique XRPD patterns, respectively.

Pharmaceutical Compositions

A composition disclosed herein includes an effective amount or a therapeutically-effective amount of a fenofibric acid salt with berberine as disclosed herein.

As one skilled in the art will ascertain, an effective amount or an amount sufficient to treat (e.g. therapeutically effective amount) refers to the amount of a pharmaceutical composition administered to improve, inhibit, or ameliorate a condition of a subject, or a symptom of a disorder, in a clinically relevant manner (e.g., improve, inhibit, or ameliorate cardiovascular diseases or conditions that can be treated by Trilipix® or other statin medications). Any improvement in the subject is considered sufficient to achieve the treatment. Preferably, an amount sufficient to treat is an amount that prevents the occurrence or one or more symptoms of the cardiovascular diseases or conditions or is an amount that reduces the severity of, or the length of time during which a subject suffers from, one or more symptoms of the cardiovascular diseases or conditions (e.g., by at least about 10%, about 20%, or about 30%, more preferably by at least about 50%, about 60%, or about 70%, and most preferably by at least about 80%, about 90%, about 95%, about 99%, or more, relative to a control subject that is not treated with a composition of the disclosure).

A sufficient amount of the pharmaceutical composition containing a fenofibric acid salt with berberine as disclosed herein used to practice the methods described herein (e.g., the treatment or prophylaxis of cardiovascular diseases or other conditions) varies depending upon the nature of the particular diseases or conditions which can be determined by standard clinical techniques, route of administration and the age, body weight, and general health of the subject being treated. Ultimately, the prescribers or researchers will decide the appropriate amount and dosage. Sometime, in vitro assays are optionally employed to help identify optimal dosage ranges. The precise dose to be employed should be decided according to the judgment of the practitioner and each subject's circumstances. However, suitable dosage ranges for oral administration are generally about 10 to 200 milligrams of active compound per day. suitable dosage ranges for intravenous administration are generally about 20 to 500 micrograms of active compound per kilogram body weight. Suitable dosage ranges for intranasal administration are generally about 0.01 pg/kg body weight to 1 mg/kg body weight. Effective doses may be extrapolated from dose response curves derived from in vitro or animal model test systems. Suppositories generally contain active ingredient in the range of 0.5% to 10% by weight; oral formulations preferably contain 10% to 95% active ingredient.

By its "pharmaceutical composition", the fenofibric acid salt with berberine or its analog as disclosed herein provides the therapeutically or biologically active agent for formulation into a suitable delivery means for administration to a subject. For the purposes of this disclosure, pharmaceutical compositions suitable for delivering the fenofibric acid salt with berberine as disclosed herein can include, e.g., tablets, gelcaps, capsules, pills, powders, granulates, suspensions, emulsions, solutions, gels, hydrogels, oral gels, pastes, eye drops, ointments, creams, plasters, drenches, delivery devices, suppositories, enemas, injectables, implants, sprays, or aerosols. Any of the aforementioned formulations can be prepared by well-known and accepted methods of art.

In an aspect, the pharmaceutical compositions disclosed herein comprise a fenofibric acid salt with berberine or its analog as disclosed herein and a pharmaceutically acceptable carrier or excipient. The term "pharmaceutically acceptable" means approved by a regulatory agency of the Federal or a state government or listed in the U.S. Pharmacopeia or other generally recognized pharmacopeia for use in animals, and more particularly in humans.

Examples of suitable pharmaceutically acceptable carriers or excipients that can be used in said pharmaceutical compositions include, but are not limited to, sugars (e.g., lactose, glucose or sucrose), starches (e.g., corn starch or potato starch), cellulose or its derivatives (e.g., sodium carboxymethyl cellulose, ethyl cellulose or cellulose acetate), oils (e.g., peanut oil, cottonseed oil, safflower oil, sesame oil, olive oil, corn oil or soybean oil), glycols (e.g., propylene glycol), buffering agents (e.g., magnesium hydroxide or aluminum hydroxide), agar, alginic acid, powdered tragacanth, malt, gelatin, talc, cocoa butter, pyrogen-free water, isotonic saline, Ringer's solution, ethanol, phosphate buffer solutions, lubricants, coloring agents, releasing agents, coating agents, sweetening, flavoring or perfuming agents, preservatives, or antioxidants.

The term "excipient" refers to additives and stabilizers typically employed in the art (all of which are termed "excipients"), including for example, buffering agents, stabilizing agents, preservatives, isotonifiers, non-ionic detergents, antioxidants and/or other miscellaneous additives. Stabilizers refer to a broad category of excipients which can range in function from a bulking agent to an additive which solubilizes the disclosed salts or helps to prevent denaturation of the same. Additional conventional excipients include, for example, fillers (e.g., starch), chelating agents (e.g., EDTA), antioxidants (e.g., ascorbic acid, methionine, vitamin E) and cosolvents.

The term "carrier" refers to a diluent, adjuvant, excipient, or vehicle with which the pharmaceutical composition is administered. Such pharmaceutical carriers are illustratively sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions are optionally employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, also contains wetting or emulsifying agents, or pH buffering agents. These compositions optionally take the form of solutions, suspensions, emulsion, tablets, pills, capsules, powders, sustained release formulations and the like. The composition is optionally formulated as a suppository, with traditional binders and carriers such as triglycerides. Oral formulation illustratively includes standard carriers such as pharmaceutical grades of mannitol, lactose, starch, magnesium stearate, sodium saccharine, cellulose, magnesium carbonate, etc.

In an aspect, pharmaceutical compositions according to the disclosure may be formulated to release the composition immediately upon administration (e.g., targeted delivery) or at any predetermined time period after administration using controlled or extended release formulations. Administration of the pharmaceutical composition in controlled or extended release formulations is useful where the composition, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in the gastro-intestinal tract; or (iii) a short biological half-life, so that frequent dosing during a day is required in order to sustain a therapeutic level. One skilled in the art will ascertain compositions for controlled or extended release of the pharmaceutical composition. In an aspect, controlled release can be obtained by controlled release compositions and coatings which are known to those of skill in the art.

Methods of Use/Treatment

A fenofibric acid salt with berberine as disclosed herein is employed in methods of therapeutic or prophylactic treatment of a subject, which may be referred to as an animal, including a human, to treat or prevent cardiovascular diseases or other conditions. As referred to herein, cardiovascular diseases or conditions include any disease state or condition can be or can be considered to be treated or prevented by Trilipix® or other statin medications.

By "treating" is meant administering a fenofibric acid salt with berberine as disclosed herein or pharmaceutical compositions containing a fenofibric acid salt with berberine as disclosed herein for prophylactic and/or therapeutic purposes. Prophylactic treatment may be administered, for example, to a subject who is not yet ill, but who is susceptible to, or otherwise at risk of, a particular disorder, e.g., cardiovascular diseases or conditions. Prophylactic treatment reduces the likelihood of a subject to develop cardiovascular diseases or conditions. Therapeutic treatment may be administered, for example, to a subject already suffering from a disorder to improve or stabilize the subject's condition. Thus, in the claims and embodiments described herein, treating is the administration to a subject either for therapeutic or prophylactic purposes. In some instances, as compared with an equivalent untreated control, treatment may ameliorate a disorder or a symptom thereof by, e.g., about 5%, about 10%, about 20%, about 30%, about 40%, about 50%, about 60%, about 70%, about 80%, about 90%, about 95%, or about 100% as measured by any standard technique. In some instances, treating can result in the inhibition of the cardiovascular diseases or conditions, the treatment of the cardiovascular diseases or conditions, and/or the amelioration of symptoms of the cardiovascular diseases or conditions. Confirmation of treatment can be assessed by detecting an improvement in or the absence of symptoms.

The methods of treatment are also meant to include the administering a therapeutically effective amount of a fenofibric acid salt with berberine as disclosed herein or pharmaceutical compositions containing a fenofibric acid salt with berberine as disclosed herein to reduce elevated low-density lipoprotein cholesterol (LDL-C), total cholesterol (Total-C), triglycerides (TG), and apolipoprotein B (Apo B), and to increase high-density lipoprotein cholesterol (HDL-C) in patients with primary hypercholesterolemia or mixed dyslipidemia. In some embodiments, the compositions containing a fenofibric acid salt with berberine as disclosed herein can reduce elevated low-density lipoprotein cholesterol (LDL-C), total cholesterol (Total-C), triglycerides (TG), and apolipoprotein B (Apo B), and to increase high-density lipoprotein cholesterol (HDL-C) in patients with primary hypercholesterolemia or mixed dyslipidemia by at least about 10%, about 20%, about 30%, about 40%, about 50%, about 60%, about 70%, about 80%, about 90%, about 95%, or more.

The methods of the disclosure may comprise, consist of or consist essentially of administering a fenofibric acid salt with berberine as disclosed herein or a pharmaceutical composition containing a fenofibric acid salt with berberine as disclosed herein to a subject in need of the cardiovascular disease or condition treatment. As used herein, by "administering" is meant a method of giving a dosage of at least one of the fenofibric acid salts with berberine as disclosed herein to an animal generally referred to as a "subject," both of which are herein understood to include human patients. The compositions utilized in the methods described herein can be administered by a route selected from, e.g., parenteral, dermal, transdermal, ocular, inhalation, buccal, sublingual, perilingual, nasal, rectal, topical administration, and oral administration or ingestion. Parenteral administration includes intravenous, intraperitoneal, subcutaneous, intraarterial, intravascular, and intramuscular administration. The preferred method of administration can vary depending on various factors (e.g., the components of the composition being administered, and the severity of the condition being treated). In a preferred aspect, the administering is by ingestion, injection, infusion, or other bodily administration.

In some embodiments, the dose of a fenofibric acid salt with berberine as disclosed herein provided to a subject in need may be administered daily, more than once daily, three times daily, every other day or in a tapered fashion depending upon various factors, including for example, nature of prophylactic versus therapeutic treatment, severity of infection being treated, the patient's overall health, and whether underlying conditions are present. It is understood that a physician would be able to monitor and adjust doses, formulations, and application methods as needed based on the patient's symptoms and responses to therapy and within the parameters and dose ranges described in the embodiments of the present disclosure.

The methods of treatment disclosed herein may be performed alone or in conjunction with another treatment. The methods of treatment may further be combined with other therapeutic agents, including for example, other statins.

The methods of treatment disclosed herein may be performed or provided to a subject, e.g., at home, the doctor's office, a clinic, a hospital's outpatient department, or a hospital. The duration of the therapy depends on the age and condition of the subject, the severity of the subject's infection, and how the subject responds to the treatment; the factors can be determined by one of skill in the art.

To prepare and manufacture the drug substance, many important factors, e.g., sources of starting materials, reaction conditions, product yields, et al., need to be carefully considered. Efforts need to be made to identify preparation methods suitable for pharmaceutical scale up and drug development.

In one aspect, disclosed herein is a fenofibric acid salt with berberine or its analogues comprising neutralized fenofibric acid as an anion and berberine or berberine analog as a cation, wherein the berberine or berberine analog has one or more of the following structures;

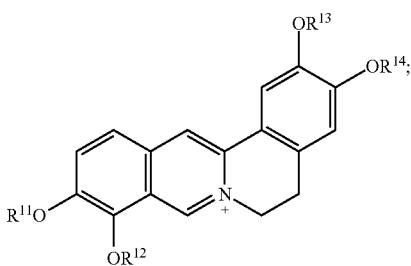

wherein $R^{11}$ and $R^{12}$ are independently H, $CH_3$, substituted or unsubstituted $C_1$-$C_3$ alkyl, or together a —$CH_2$— or substituted —$CH_2$— group; and $R^{13}$ and $R^{14}$ are independently H, CH$_3$, substituted or unsubstituted C$_1$-C$_3$ alkyl, or together a —CH$_2$— or substituted —CH$_2$— group;

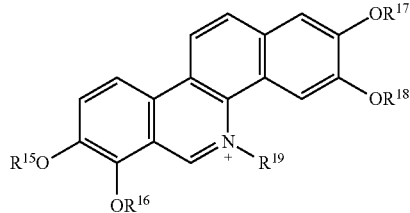

wherein R$^{15}$ and R$^{16}$ are independently H, CH$_3$, substituted or unsubstituted C$_1$-C$_3$ alkyl, or together a —CH$_2$— or substituted —CH$_2$— group; R$^{17}$ and R$^{18}$ are independently H, CH$_3$, substituted or unsubstituted C$_1$-C$_3$ alkyl, or together a —CH$_2$— or substituted —CH$_2$— or substituted —CH$_2$— group; and R$^{19}$ is H, O, CH$_3$, substituted or unsubstituted C$_1$-C$_3$ alkyl;

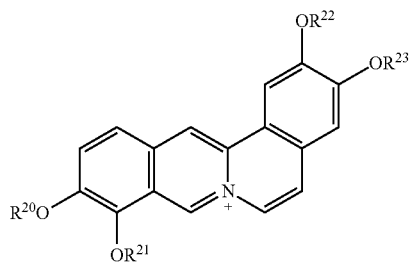

wherein R$^{20}$ and R$^{21}$ are independently H, CH$_3$, substituted or unsubstituted C$_1$-C$_3$ alkyl, or together a —CH$_2$— or substituted —CH$_2$— group; and R$^{22}$ and R$^{23}$ are independently H, CH$_3$, substituted or unsubstituted C$_1$-C$_3$ alkyl, or together a —CH$_2$— or substituted —CH$_2$— group; and

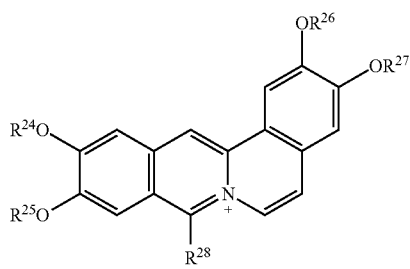

wherein R$^{24}$ and R$^{25}$ are independently H, substituted or unsubstituted C$_1$-C$_3$ alkyl, or together a —CH$_2$— or substituted —CH$_2$— group; and R$^{26}$ and R$^{27}$ are independently H, substituted or unsubstituted C$_1$-C$_3$ alkyl, or together a —CH$_2$— or substituted —CH$_2$— group; R$^{28}$ is H, substituted or unsubstituted C$_1$-C$_3$ alkyl, —OH, —OCH$_3$, or OCH$_2$CH$_3$.

In some embodiments, the salt disclosed herein is in amorphous form, crystalline form, polymorph form, anhydrous form, hydrate, solvate, co-crystal, or a mixture thereof.

In some other embodiments, the salt disclosed herein is in crystalline form. In some embodiments, the salt disclosed herein is in polymorph form.

In some other embodiments, the cation in the disclosed salts comprises berberine. In some other embodiments, the cation in the disclosed salts comprises a berberine analog as cation. In yet some other embodiments, the cation in the disclosed salts comprises

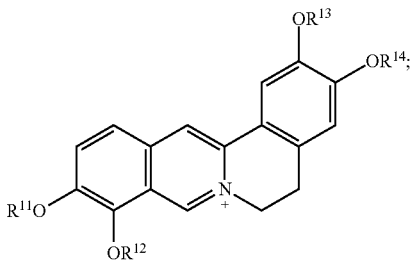

wherein R$^{11}$ and R$^{12}$ are independently H, CH$_3$, substituted or unsubstituted C$_1$-C$_3$ alkyl, or together a —CH$_2$— or substituted —CH$_2$— group; and R$^{13}$ and R$^{14}$ are independently H, CH$_3$, substituted or unsubstituted C$_1$-C$_3$ alkyl, or together a —CH$_2$— or substituted —CH$_2$— group.

In some embodiments, the cation in the disclosed salts comprises

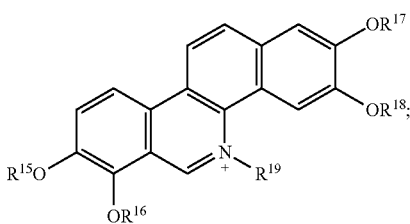

wherein R$^{15}$ and R$^{16}$ are independently H, CH$_3$, substituted or unsubstituted C$_1$-C$_3$ alkyl, or together a —CH$_2$— or substituted —CH$_2$— group; R$^{17}$ and R$^{18}$ are independently H, CH$_3$, substituted or unsubstituted C$_1$-C$_3$ alkyl, or together a —CH$_2$— or substituted —CH$_2$— group; and R$^{19}$ is H, O, CH$_3$, substituted or unsubstituted C$_1$-C$_3$ alkyl.

In some other embodiments, the cation in the disclosed salts comprises

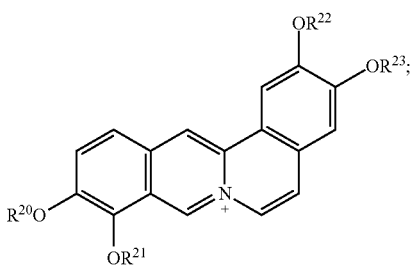

wherein R$^{20}$ and R$^{21}$ are independently H, CH$_3$, substituted or unsubstituted C$_1$-C$_3$ alkyl, or together a —CH$_2$— or substituted —CH$_2$— group; and R$^{22}$ and R$^{23}$ are independently H, CH$_3$, substituted or unsubstituted C$_1$-C$_3$ alkyl, or together a —CH$_2$— or substituted —CH$_2$— group.

In some other embodiments, the cation in the disclosed salts comprises

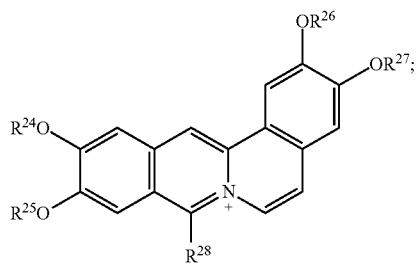

wherein $R^{24}$ and $R^{25}$ are independently H, substituted or unsubstituted $C_1$-$C_3$ alkyl, or together a —$CH_2$— or substituted —$CH_2$— group; and $R^{26}$ and $R^{27}$ are independently H, substituted or unsubstituted $C_1$-$C_3$ alkyl, or together a —$CH_2$— or substituted —$CH_2$— group; $R^{28}$ is H, substituted or unsubstituted $C_1$-$C_3$ alkyl, —OH, —$OCH_3$, —$OCH_2CH_3$.

In some embodiments, the cation in the disclosed salts comprises a mixture of berberine and one of its analogs. In some other embodiments, the cation in the disclosed salts comprises berberine and two or more of its analogs. In yet some other embodiments, the cation in the disclosed salts comprises one, two, or more berberine analogs.

In yet some other embodiments, the cation in the disclosed salts comprises berberine alone. In some embodiments, the disclosed salts are free of choline, tromethamine, calcium, diethanolamine, lysine, piperazine, ethanolamine, meglumine, sodium, chlorine, sulfate, halogen ion, or combination thereof. In some embodiments, the disclosed salts are free of choline, chlorine, or a combination thereof.

In some embodiments, the cation in the disclosed salts comprises one or more of berberine analogs.

In some embodiments, the cation in the disclosed salts comprises one or more of

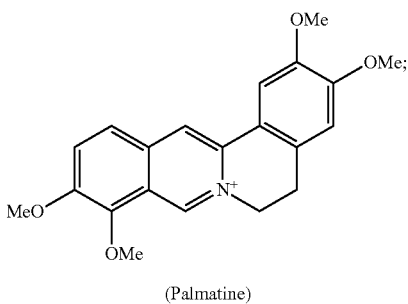

(Palmatine)

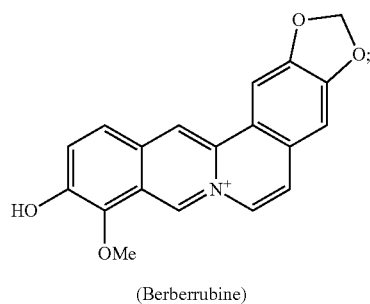

(Berberrubine)

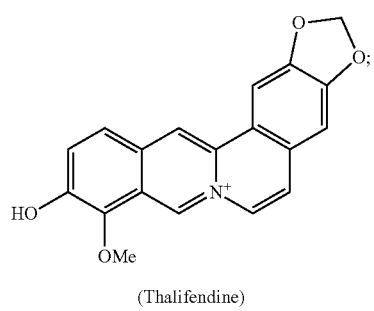

(Thalifendine)

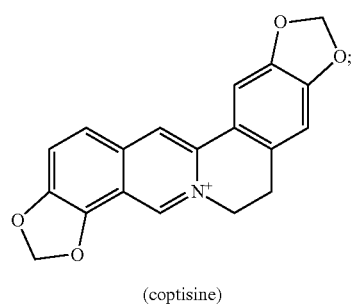

(coptisine)

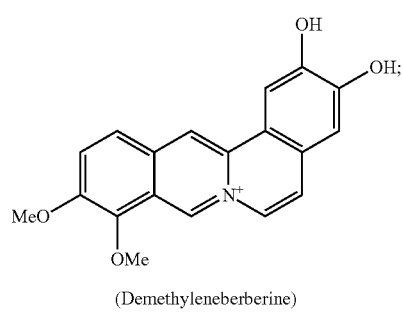

(Demethyleneberberine)

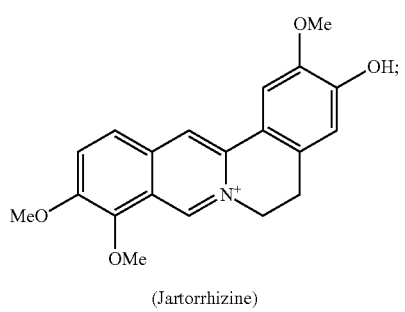

(Jartorrhizine)

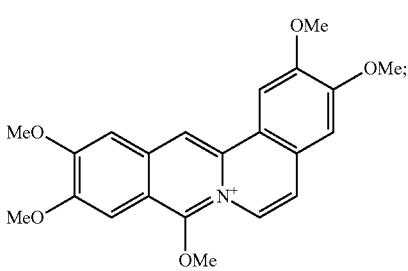

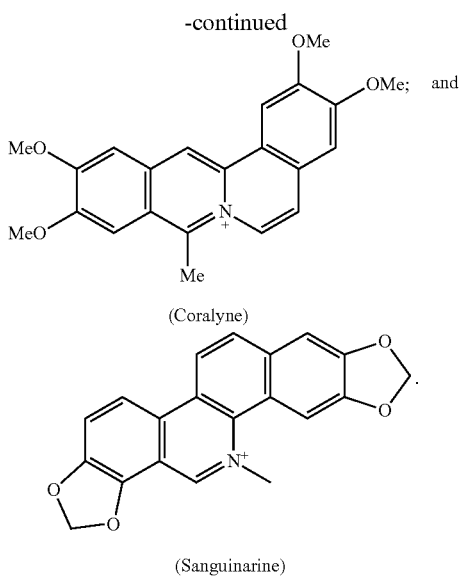

(Coralyne)

(Sanguinarine)

In some embodiments, the salts disclosed herein have a molar ratio of the neutralize fenofibric acid and berberine or berberine analog of from about 1:2 to about 2:1, preferably about 1:1. In some other embodiments, the molar ratio between the neutralize fenofibric acid and berberine or berberine analog of the salts disclosed herein is from about 0.95:1 to about 1:0.95, from about 0.9:1 to about 1:0.9, from about 0.8:1 to about 1:0.8, from about 0.7:1 to about 1:0.7, from about 0.6:1 to about 1:0.6, from about 0.5:1 to about 1:0.5, or any value there between.

In some embodiments, the salts disclosed herein are of single crystalline form. In some other embodiments, the salts disclosed herein are mixtures of multiple crystalline forms.

In some embodiments, the salt disclosed herein is a fenofibric acid salt with berberine, in crystalline form, and characterized by an XRPD pattern comprising one or more peaks expressed as 2θ±0.2° of about 6.1°, about 7.8°, about 12.2°, about 15.6°, about 17.3°, about 18.3°, about 18.6°, about 19.6°, about 20.4°, and about 25.4°.

In some other embodiments, the salt disclosed herein is a fenofibric acid salt with berberine, in crystalline form, and characterized by an XRPD pattern comprising one or more peaks expressed as 2θ±0.2° of about 6.2°, about 8.0°, about 12.4, about 12.9°, about 15.9°, about 17.3°, about 18.7°, about 19.8°, about 20.9°, and about 25.5°.

In some embodiments, the salt disclosed herein is a fenofibric acid salt with berberine, in crystalline form, and characterized by an XRPD pattern comprising one or more peaks expressed as 2θ±0.2° of about 6.0°, about 7.7°, about 12.1°, about 15.5°, about 18.2°, about 18.5°, about 19.5°, about 20.3°, about 25.7°, and about 32.0°.

In some embodiments, the salt disclosed herein is a fenofibric acid salt with berberine, in crystalline form, and characterized by an XRPD pattern comprising one or more peaks expressed as 2θ±0.2° of about 5.5°, about 6.9°, about 7.8°, about 9.7°, about 15.7°, about 15.9°, about 17.0°, about 19.2°, about 20.0°, and about 21.3°.

In some embodiments, the salt disclosed herein is a fenofibric acid salt with berberine, in crystalline form, and characterized by an XRPD pattern comprising one or more peaks expressed as 2θ±0.2° of about 7.9°, about 13.1°, about 15.8°, about 16.9°, about 17.7°, about 20.7°, about 26.1°, about 26.4°, about 27.0°, and about 27.6°.

In some embodiments, the salt disclosed herein is a fenofibric acid salt with berberine, in crystalline form, and characterized by an XRPD pattern comprising one or more peaks expressed as 2θ±0.2° of about 5.3°, about 5.6°, about 6.6°, about 8.4°, about 14.0°, about 17.6°, about 19.2°, about 23.4°, about 25.1°, and about 25.7°.

In some embodiments, the salt disclosed herein is a fenofibric acid salt with berberine, in crystalline form, and characterized by an XRPD pattern comprising one or more peaks expressed as 2θ±0.2° of about 6.1°, about 7.8°, about 12.1°, about 12.3°, about 12.9°, about 13.8°, about 15.8°, about 17.3°, about 19.7°, and about 20.8°.

In some embodiments, the salt disclosed herein is a fenofibric acid salt with berberine, in crystalline form, and characterized by an XRPD pattern comprising one or more peaks expressed as 2θ±0.2° of about 5.5°, about 6.5°, about 8.0°, about 8.3°, about 10.9°, about 12.9°, about 14.0°, about 17.5°, about 17.9°, about 22.0°, and about 23.2°.

In some embodiments, the salt disclosed herein further comprises a solvate, hydrate, co-crystal, or mixture thereof.

In some embodiments, the salt disclosed herein is a crystalline solid and non-hygroscopic. In some other embodiments, the salt disclosed herein is a crystalline solid and anhydrous.

In another aspect, disclosed herein is a composition comprising one or more salts disclosed herein and a pharmaceutically acceptable carrier.

In some embodiments, the carrier of the compositions disclosed herein is a diluent, adjuvant, excipient, and vehicle. In some other embodiments, the carrier is an excipient.

In some embodiments, the composition disclosed herein is formulated into tablets, gelcaps, capsules, pills, powders, granulates, suspensions, emulsions, solutions, gels, hydrogels, oral gels, pastes, eye drops, ointments, creams, plasters, drenches, delivery devices, suppositories, enemas, injectables, implants, sprays, or aerosols.

In some embodiments, the composition is an immediate release composition. In some other embodiments, the composition is an extended release composition.

In some embodiments, the disclosed compositions are free of choline, tromethamine, calcium, diethanolamine, lysine, piperazine, ethanolamine, meglumine, sodium, chlorine, sulfate, halogen ion, or combination thereof. In some embodiments, the disclosed composition is free of choline, chlorine, or a combination thereof.

In yet another aspect, disclosed herein is a method of therapeutic or prophylactic treatment of a subject against cardiovascular diseases or other conditions, the method comprises administering a therapeutically effective amount of a fenofibric acid salt with berberine or its analog disclosed herein to a subject in need of cardiovascular disease or other condition care.

In some embodiments, the administering of the disclosed method is by ingestion or other routes.

In another aspect, disclosed herein is a method for preparing a salt disclosed herein, wherein the method comprises mixing berberine hydroxide or a mixture of berberine salt with a hydroxide with fenofibric acid or salt thereof.

In yet another aspect, disclosed herein is a method for preparing a berberine salt of an active pharmaceutical agent, wherein the method comprises mixing berberine hydroxide or a mixture of berberine salt with a hydroxide with an active pharmaceutical agent or its salt thereof, wherein the active pharmaceutical agent is capable to form an anion and form a salt with berberine or its analog.

In another aspect, disclosed herein is a method for preparing a crystalline fenofibric acid salt with berberine, wherein the method comprises converting a fenofibric acid salt with berberine analog in any solid form to a crystalline fenobibric acid salt berberine or its analog by heating or using a solvent or solvent mixture.

The salts and methods disclosed herein can be used to improve pharmaceutical properties, including crystallinity, chemical purity, stability, solid-state properties, solubility, dissolution rate, particle and powder properties, or manufacturability.

As used herein, the term "substantially free", "free" or "free of" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions of the present disclosure may comprise, consist essentially of, or consist of the components and ingredients of the disclosed compositions or methods as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

All publications, patent applications, issued patents, and other documents referred to in this specification are indicative of the level of ordinary skill in the art to which this disclosure pertains and are herein incorporated by reference to the same extent as if each individual publication or patent application was specifically and individually indicated as incorporated by reference. Definitions that are contained in text incorporated by reference are excluded to the extent that they contradict definitions in this disclosure.

The present disclosure is further illustrated by the following examples, which should not be considered as limiting in any way.

EXAMPLES

Embodiments of the present disclosure are further defined in the following non-limiting Examples. It should be understood that these Examples, while indicating certain embodiments of the disclosure, are given by way of illustration only. From the above discussion and these Examples, one skilled in the art can ascertain the essential characteristics of this disclosure, and without departing from the spirit and scope thereof, can make various changes and modifications of the embodiments of the disclosure to adapt it to various usages and conditions. Thus, various modifications of the embodiments of the disclosure, in addition to those shown and described herein, will be apparent to those skilled in the art from the foregoing description. Such modifications are also intended to fall within the scope of the appended claims.

Chemicals and Analytic Method

Chemicals

All the compounds, including fenofibric acid, berberine chloride, berberine hemisulfate, and the solvents used in the experiments, were purchased from Sigma-Aldrich and used without further purification.

Analytical Methods

Nuclear Magnetic Resonance (NMR) Spectroscopy

In general, the structures of end-products of the salt were confirmed by nuclear magnetic resonance (NMR) spectroscopy. Proton magnetic resonance spectra were taken using a Bruker Avance 500 (500 MHz) or Bruker Avance 300 (300 MHz)] and NMR chemical shift values were given in ppm. Proton NMR measurements were taken at ambient temperature unless otherwise specified; the following abbreviations have been used for characterizing NMR peaks: s, singlet; d, doublet; t, triplet; q, quartet; m, multiplet; dd, doublet of doublets; ddd, doublet of doublet of doublet; dt, doublet of triplets; bs, broad signal. The chemical shifts ($\delta$) of the NMR peak are reported in parts per million (ppm) downfield of tetramethylsilane (TMS) and referenced to the respective residual un-deuterated solvent peak as follows: $CDCl_3$=7.26 ppm, $MeOH-d_4$=3.31 ppm for $^1$H-NMR; and $CDCl_3$=77.0 ppm, $MeOH-d_4$=49.00 ppm for $^{13}$C-NMR. Apparent coupling constants (J) are reported in Hz.

Single Crystal X-Ray Analysis

Single crystal X-ray analysis provides detail information at the molecular level and demonstrates the formation of salt. Single crystal X-ray analysis was performed using a Bruker Apex diffractometer made by Bruker AXS Inc™ (Madison, Wis.). The X-ray (diffraction) data were collected at 23° C. on Mo source. The crystal structure was solved and refined with the SHELXTL package. All the hydrogen atoms were calculated.

X-Ray Powder Diffraction (XRPD) Analysis

In general, the crystalline forms of the salts were analyzed by X-ray powder diffraction (XRPD), which provides a finger print of a crystalline form. XRPD analysis was performed using a Bruker D8 diffractometer by Bruker AXS Inc™ (Madison, Wis.). The XRPD spectra were obtained by mounting a sample (approximately 10 mg) of the material for analysis on a single silicon crystal wafer mount (e.g., a Bruker silicon zero background X-ray diffraction sample holder) and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5406 angstroms (e.g., about 1.54 angstroms). The sample was exposed for 1 second per 0.02 degree 2-theta increment (continuous scan mode) over the range 5 degrees to 40 degrees 2-theta in theta-theta mode. The running time was ~15 min for such a measurement.

XRPD 2θ values may vary with a reasonable range, e.g., in the range±0.2° and the XRPD intensities may vary when measured for essentially the same crystalline form for a variety of reasons including, for example, preferred orientation.

Differential Scanning Calorimetry (DSC) Analysis

DSC analysis was performed on samples prepared according to standard methods using a Q SERIES™ Q1000 DSC calorimeter available from TA INSTRUMENTS® (New Castle, Del.). A sample (approximately 2 mg) was weighed into an aluminum sample pan and transferred to the DSC. The instrument was purged with nitrogen at 50 mL/min and data collected between 22° C. and 300° C., using a dynamic heating rate of 10° C./minute. Thermal data was analyzed using standard software, e.g., Universal v.4.5A from TA INSTRUMENTS®.

Thermogravimetry Analysis (TGA)

TGA was performed on samples prepared according to standard methods using a Q SERIES™ Q5000 thermogravimetry analyzer available from TA Instruments INSTRUMENTS® (New Castle, Del.). A sample (approximately 5 mg) was placed into an aluminum sample pan and transferred to the TGA furnace. The instrument was purged with nitrogen at 50 mL/min and data collected between 25° C. and 300° C., using a dynamic heating rate of 10° C./minute. Thermal data was analyzed using standard software, e.g., Universal v.4.5A from TA INSTRUMENTS®.

Example 1

Preparation and Characterization of an Exemplary Berberine Salt of Fenofibric Acid (Form A Salt)

74.2 mg (0.20 mmol) of berberine chloride was suspended in 1.0 ml of MeOH, and then 2.0 ml of 0.1 N NaOH (0.2 mmol) was added to produce a suspension. 64.1 mg (0.20 mmol) of fenofibric acid was added to the suspension. A clear orange solution was obtained after the suspension was stirred at 60° C. for 30 minutes. The solution was cooled down to the ambient temperature and a yellow berberine salt of fenofibric acid (Form A salt) was precipitated out from the orange solution. Form A salt was separated by filtration, washed with water, and then dried in the air. 83.2 mg of Form A salt was obtained (60% yield).

The proton NMR spectrum of Form A salt in $D_2O$, shown in FIG. 1, indicates a about 1:1 ratio of berberine and fenofibric acid for Form A salt. $^1H$ NMR (300 MHz, DMSO) 1.41 (s, 6H), 3.21 (t, J=6.0 Hz, 2H), 4.07 (s, 3H), 4.10 (s, 3H), 4.94 (t, J=6.0 Hz, 2H), 6.18 (s, 2H), 6.86-6.91 (m, 2H), 7.09 (s, 1H), 7.56-7.61 (m, 4H), 7.66-7.71 (m, 2H), 7.80 (s, 1H), 8.00 (d, J=9.0 Hz, 1H), 8.20 (d, J=9.0 Hz, 1H), 8.94 (s, 1H), 9.89 (s, 1H).

Figure 2:
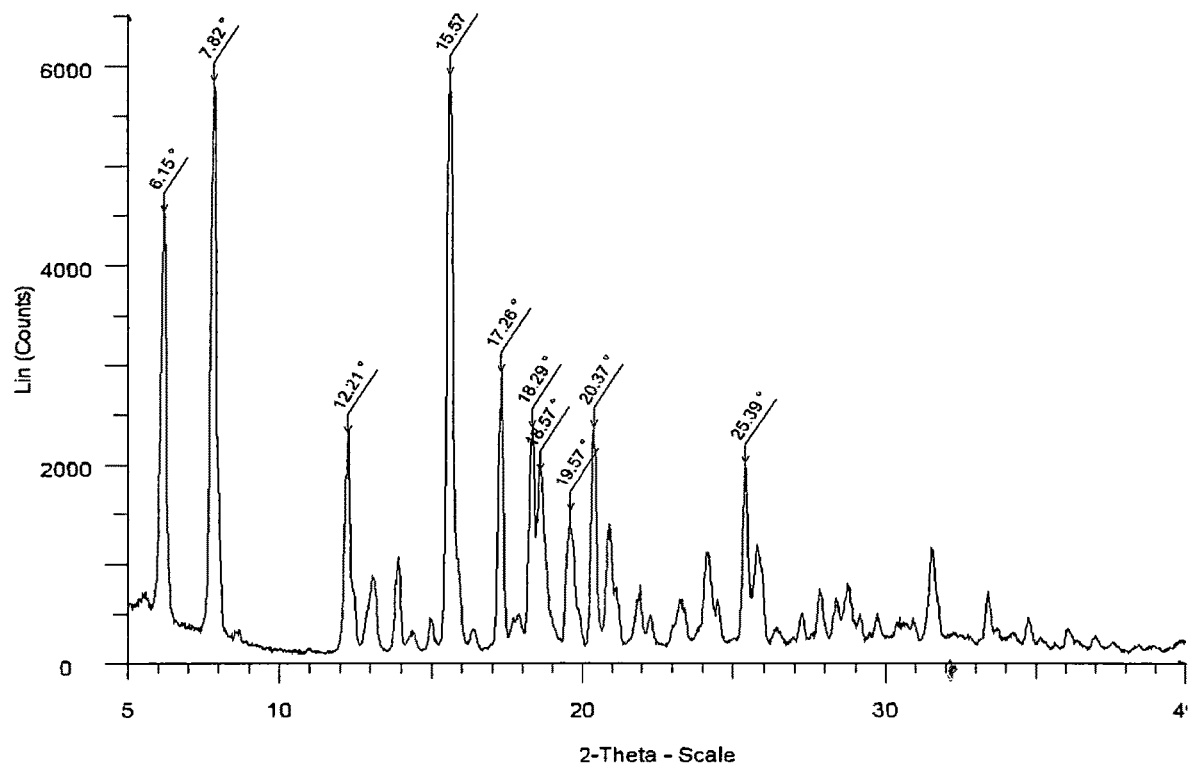
FIG. 2 shows the powder X-ray diffraction pattern of a fenofibric acid salt with berberine (Form A salt).

Form A salt was analyzed by XRPD. The key peaks from the XRPD analysis are tabulated in Table 1 and the XRPD pattern is shown in FIG. 2.

Table 1. XRPD Peaks for Form A

| Angle (2θ ± 0.2°) | Intensity (%) |
|---|---|
| 15.6 | 100.0 |
| 7.8 | 98.8 |
| 6.1 | 76.7 |
| 17.3 | 49.6 |
| 18.3 | 40.2 |
| 20.4 | 40.2 |
| 12.2 | 39.2 |
| 25.4 | 34.1 |
| 18.6 | 32.9 |
| 19.6 | 25.9 |

Figure 3:
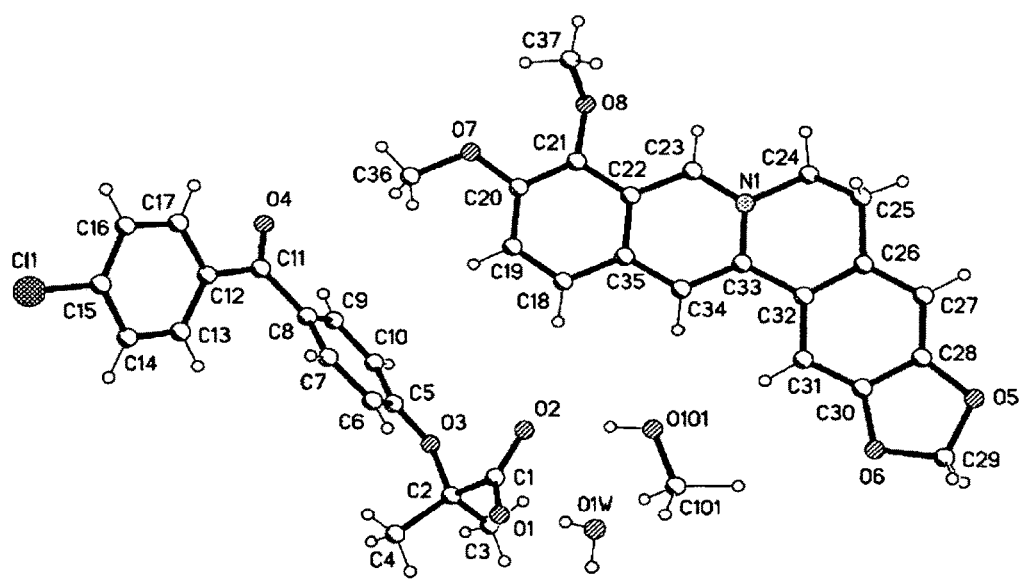
FIG. 3 shows the crystal structure of a fenofibric acid salt with berberine (Form A salt).

Single crystals of Form A salt were obtained by slow evaporation of the MeOH solution of Form A salt. Single crystal analysis confirms Form A salt (1:1 counter ion ratio) is a mono MeOH solvate of monohydrate. Single crystal structure of Form A is shown in FIG. 3. Crystallographic data: space group triclinic P-1, unit cell dimensions: a=7.0792(4) Å, b=14.6702(7) Å, c=16.3544(8) Å, α=83.881(2) °, β=83.306(2) °, γ=87.352(2) °, and V=1676.29(15) Å$^3$.

A simulated powder X-ray diffraction pattern calculated from the single crystal structure of Form A salt matches with the experimental powder X-ray diffraction pattern of Form A salt bulk material.

Example 2

Preparation of an Exemplary Berberine Salt of Fenofibric Acid (Form B Salt)

100 mg of a berberine salt of fenofibric acid (Form A salt, other amorphous, or crystalline forms) was suspended in 1.0 ml of water to produce a suspension. The suspension was then stirred at the ambient condition for 1 day. The solid was collected by filtration and dried in air. 75 mg of yellow crystalline material of Form B salt was obtained. (Yield: 75%).

Figure 4:
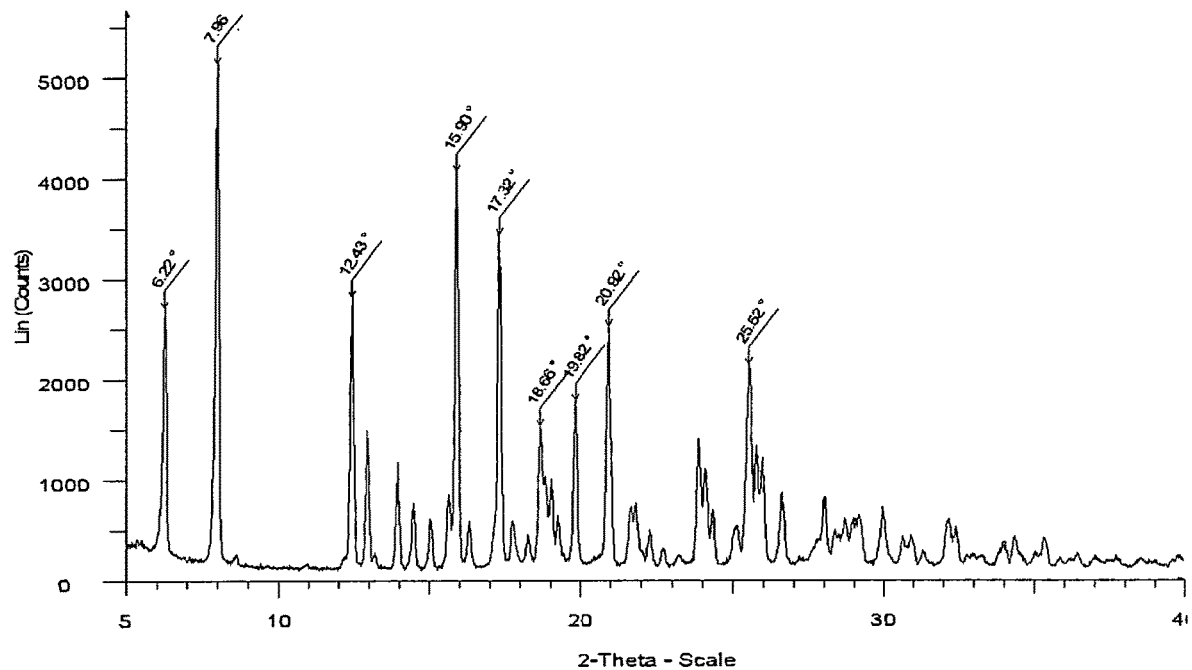
FIG. 4 shows the powder X-ray diffraction pattern of another fenofibric acid salt with berberine (Form B salt).

Form B was analyzed by XRPD and the results are tabulated in Table 2. The XRPD for Form B salt is shown in FIG. 4.

Table 2. XRPD Peaks for Form B

| Angle (2θ ± 0.2°) | Intensity (%) |
|---|---|
| 8.0 | 100.0 |
| 15.9 | 79.1 |
| 17.3 | 67.0 |
| 12.4 | 55.0 |
| 6.2 | 52.9 |
| 20.9 | 49.2 |
| 25.5 | 41.8 |
| 19.8 | 34.8 |
| 18.7 | 30.0 |
| 12.9 | 28.9 |

Form B salt is characterized in exhibiting at least one of the following 2θ±0.2° values measured using CuKα radiation: 6.2, 12.4, and 20.9°.

Figure 5:
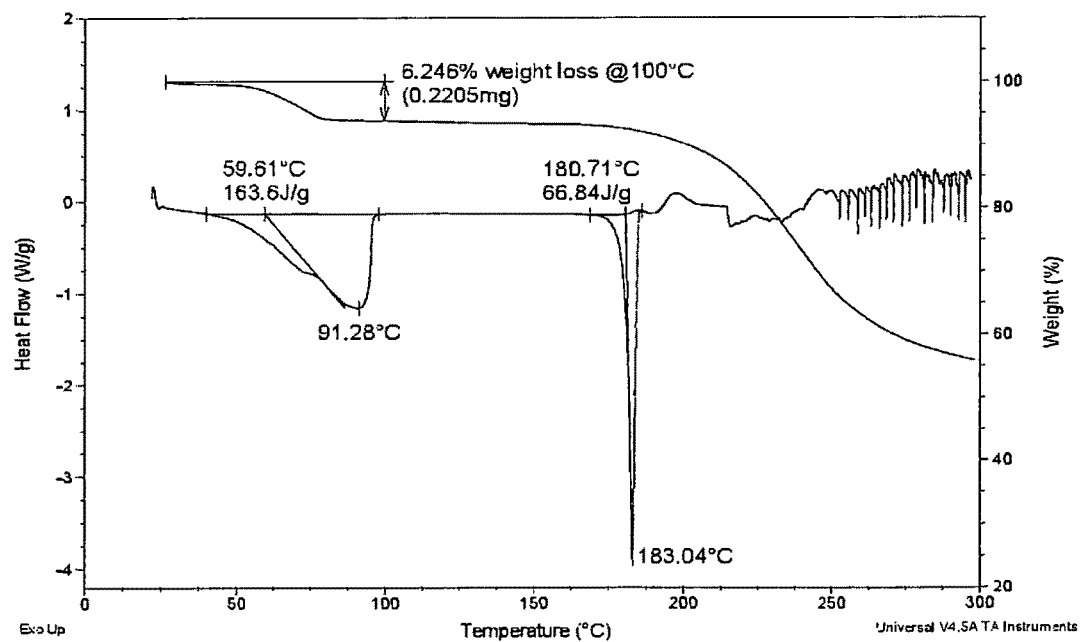
FIG. 5 shows DSC/TGA diagrams of another fenofibric acid salt with berberine (Form B salt).

Form B salt was also analyzed by thermal techniques. DSC analysis indicated that Form B salt had an endotherm event of de-solvation with an onset at about 60° C. and a peak at about 91° C., followed by a melting point with an onset at about 181° C. and a peak at about 183° C. TGA indicated that Form B salt exhibited a mass loss of about 6.2% upon heating from about 25° C. to about 100° C. A representative DSC/TGA thermogram of Form B salt is shown in FIG. 5.

Example 3

Preparation of an Exemplary Berberine Salt of Fenofibric Acid (Form C Salt)

318.2 mg of fenofibric acid (1.0 mmol) was suspended in 5.0 ml of water and 1.0 ml of 1 N NaOH aqueous solution was added to get a clear colorless solution. 384.7 mg of berberine hemisulfate salt (1.0 mmol) was dissolved in 10.0 ml of water to get a clear orange solution. The colorless solution of fenofibric acid and NaOH was slowly added to the orange solution of berberine, the yellow solid precipitated out first and then a bilayer solution was formed. 5.0 ml of ethanol was added to the bilayer solution, a yellow crystalline Form C salt solid started to precipitate out and the slurry was stirred at the ambient temperature for 1 day. 530 mg of yellow crystalline material of Form C salt was obtained (Yield: 82%).

Figure 6:
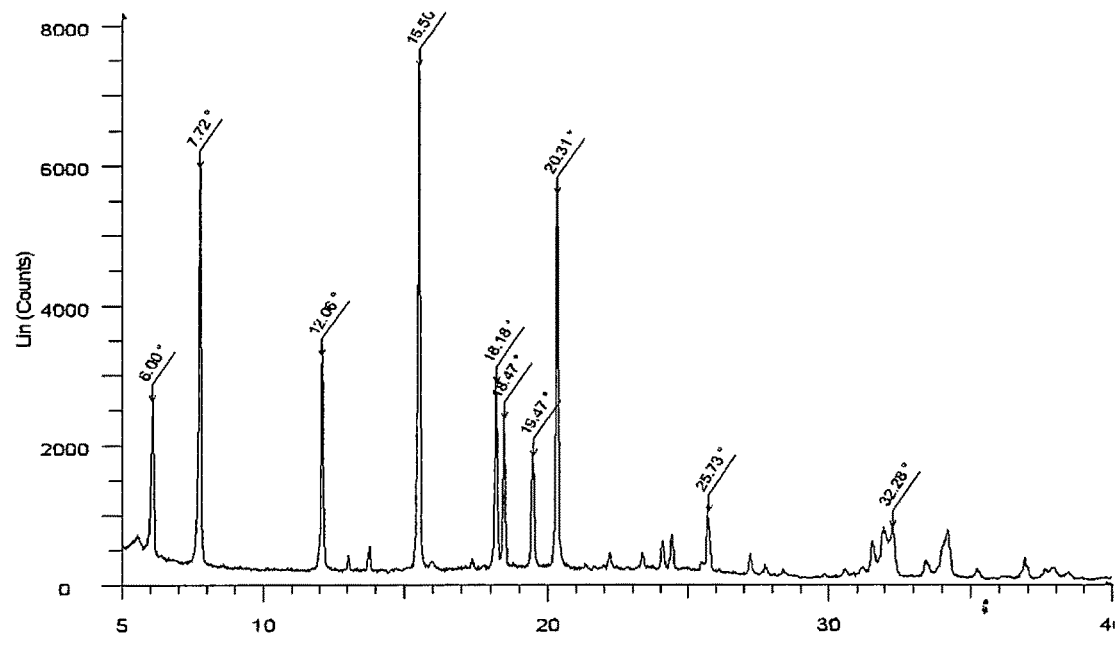
FIG. 6 shows the powder X-ray diffraction pattern of another fenofibric acid salt with berberine (Form C salt).

Form C was analyzed by XRPD. The XRPD pattern of Form C is shown in FIG. 6 and the results are tabulated in Table 3.

Table 3. XRPD Peaks for Form C Salt

| Angle (2θ ± 0.2°) | Intensity (%) |
|---|---|
| 15.5 | 100.0 |
| 7.7 | 80.5 |
| 20.3 | 75.3 |
| 12.1 | 44.1 |
| 18.2 | 38.9 |
| 6.0 | 35.4 |
| 18.5 | 32.0 |
| 19.5 | 24.8 |
| 25.7 | 14.1 |
| 32.3 | 11.0 |

Example 4

Preparation of an Exemplary Berberine Salt of Fenofibric Acid (Form D Salt)

159.4 mg (0.50 mmol) of fenofibric acid was dissolved in 5.0 ml of 0.1 N NaOH (0.5 mmol) aqueous solution to produce a solution. 185.9 (0.50 mmol) of berberine chloride was added to the solution to get a suspension. 5 ml of MeOH was added to the suspension and the suspension was heated to 60° C. to get a clear dark orange solution. The solution was filtered and evaporated in the ambient temperature.

The solution was condensed to ~2 ml and a yellow solid was precipitated to produce a suspension. 3 ml of extra water was added to the suspension, and the slurry was stirred for 1 days. The solid was filtered and washed with water to yield Form D salt. Form D salt was then dried in the oven at 40° C. with vacuum for 12 hours. 254.0 mg of yellow crystalline Form D salt was obtained (Yield: 78%).

Form D can also be prepared by heating crystalline forms, Form A, Form B, Form C or other forms, or slurry in EtOAc or other solvents.

Figure 7:
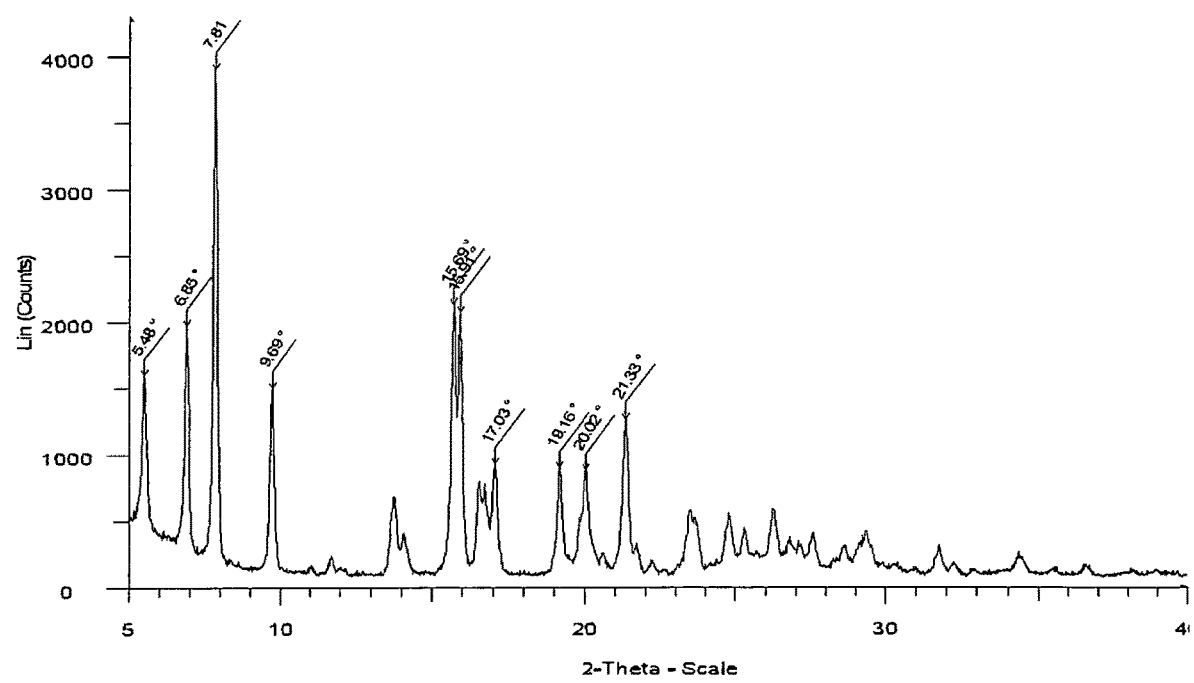
FIG. 7 shows the powder X-ray diffraction pattern of another fenofibric acid salt with berberine (Form D salt).

Form D was analyzed by XRPD. The XRPD pattern is shown in FIG. 7 and the results are tabulated in Table 4.

Table 4. XRPD Peaks for Form D Salt

| Angle (2θ ± 0.2°) | Intensity (%) |
|---|---|
| 7.8 | 100.0 |
| 15.7 | 54.6 |
| 15.9 | 53.1 |
| 6.9 | 50.4 |
| 5.5 | 40.8 |
| 9.7 | 38.5 |
| 21.3 | 32.3 |
| 17.0 | 23.7 |
| 19.2 | 23.0 |
| 20.0 | 22.5 |

Form D salt is characterized in exhibiting at least one of the following 2θ±0.2° values measured using CuKα radiation: 5.4, 6.8, and 9.7°.

Figure 8:
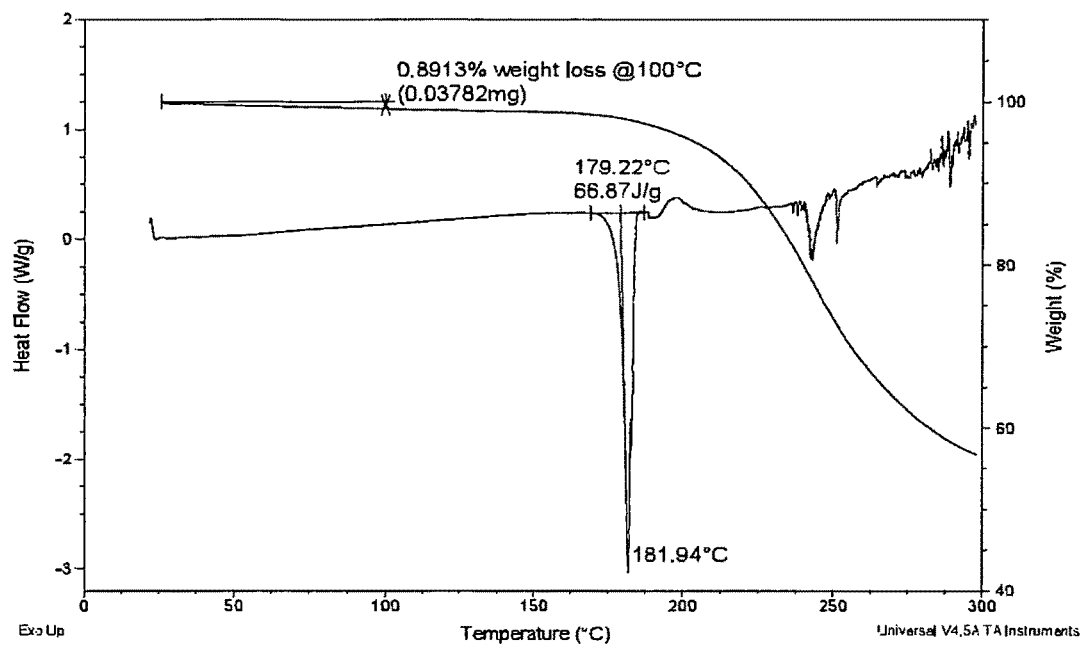
FIG. 8 shows the DSC/TGA diagrams of another fenofibric acid salt with berberine (Form D salt).

Form D salt was analyzed by thermal techniques. A representative DSC/TGA thermogram of Form D salt is shown in FIG. 8. DSC analysis indicated that Form D salt had an endotherm event of a melting point with an onset at about 179° C. and a peak at about 182° C. TGA indicated that Form D salt exhibited a mass loss of about 0.9% upon heating from about 25° C. to about 100° C.

Example 5

Preparation of an Exemplary Berberine Salt of Fenofibric Acid (Form E Salt)

317.9 mg of fenofibric acid (1.0 mmol) was suspended in 4.0 ml of water and 1.0 ml of 1 N NaOH aqueous solution was added to get a clear colorless solution. 371.9 mg of berberine chloride (1.0 mmol) was dissolved in 12.0 ml of hot water. The hot solution of sodium fenofibrate in water was slowly added to the berberine solution. The yellow precipitate was formed. The suspension was cooled down to the ambient temperature and stirred for another 1 hour to get a bilayer solution. 2.0 ml of ethanol was added to the bilayer solution, yellow solid started to precipitate out. The slurry was stirred at the ambient temperature for 1 day. The solid was filtered and washes with water. 530.0 mg of yellow crystalline material of Form E was obtained. (Yield: 82%).

Figure 9:
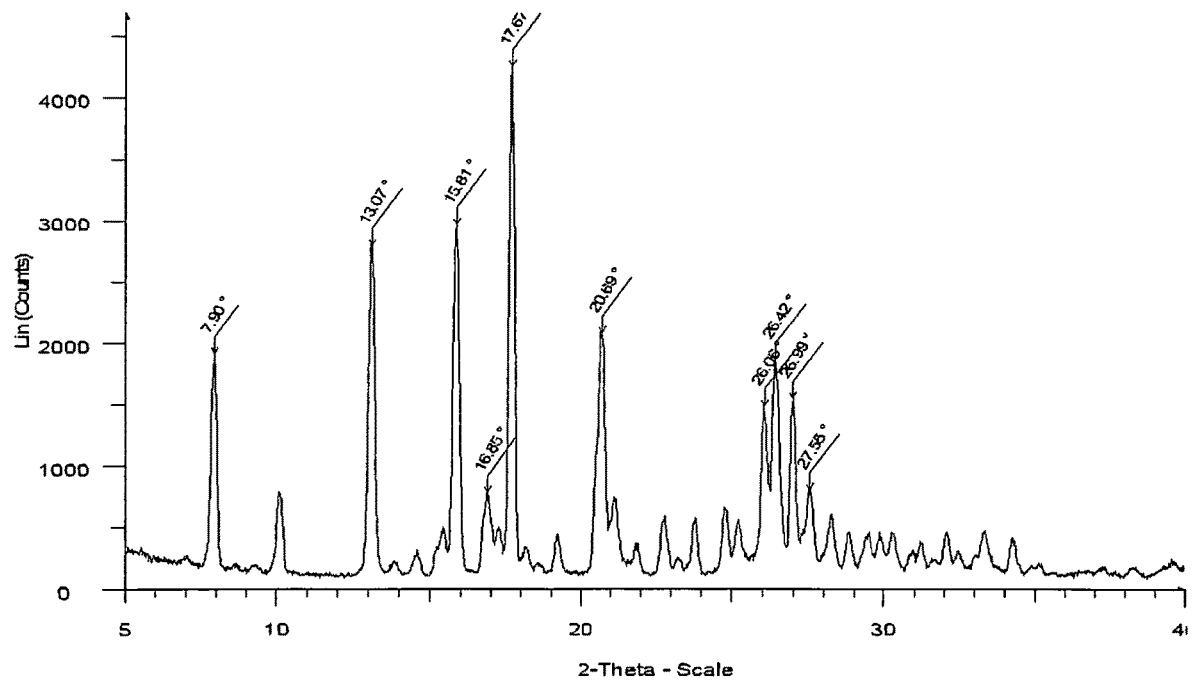
FIG. 9 shows the powder X-ray diffraction pattern of another fenofibric acid salt with berberine (Form E salt).

Form E salt was analyzed by XRPD. The XRPD pattern of Form E salt is shown in FIG. 9 and the results are tabulated in Table 5.

Table 5. XRPD Peaks for Form E

| Angle (2θ ± 0.2°) | Intensity (%) |
|---|---|
| 17.7 | 100.0 |
| 15.8 | 69.7 |
| 13.1 | 65.9 |
| 20.7 | 48.9 |
| 7.9 | 45.0 |
| 26.4 | 43.9 |
| 27.0 | 36.3 |
| 26.1 | 34.9 |
| 27.6 | 18.9 |
| 16.9 | 18.4 |

Example 6

Preparation of an Exemplary Berberine Salt of Fenofibric Acid (Form F Salt)

100.2 mg of Form E salt was heated to 100° C. for 1 hour. A new crystalline form of the berberine salt of fenofibric acid, Form F salt, was obtained.

Figure 10:
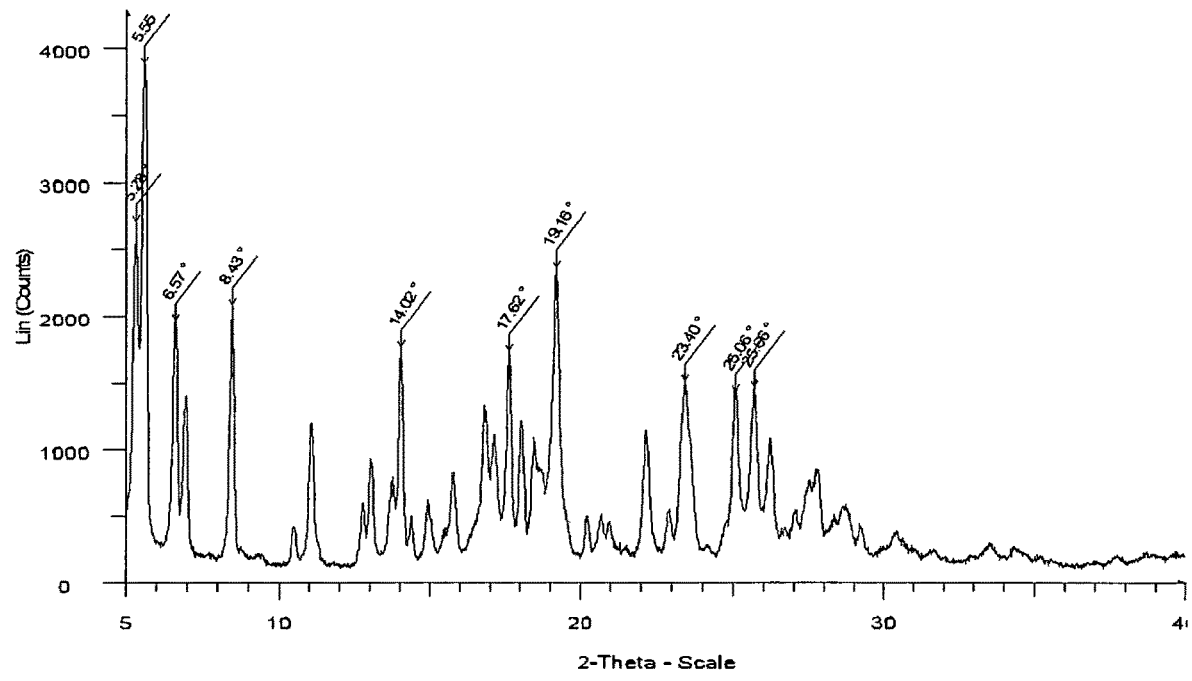
FIG. 10 shows the powder X-ray diffraction pattern of another fenofibric acid salt with berberine (Form F salt).

Form F was analyzed by XRPD. The XRPD pattern of Form F salt is shown in FIG. 10 and the results are tabulated in Table 6.

Table 6. XRPD Peaks for Form F

| Angle (2θ ± 0.2°) | Intensity (%) |
|---|---|
| 5.6 | 100.0 |
| 5.3 | 69.6 |
| 19.2 | 60.9 |
| 8.4 | 53.6 |
| 6.6 | 50.7 |
| 14.0 | 45.4 |
| 17.6 | 44.6 |
| 23.4 | 38.9 |
| 25.7 | 37.7 |
| 25.1 | 36.9 |

Example 7

Preparation of an Exemplary Berberine Salt of Fenofibric Acid (Form G Salt)

20.2 mg of Form E salt of fenofibric acid was dissolved in 0.5 ml of isopropanol and 0.5 ml of water. The clear yellow solution was evaporated to dry, and a yellow powder of Form G salt was obtained.

Figure 11:
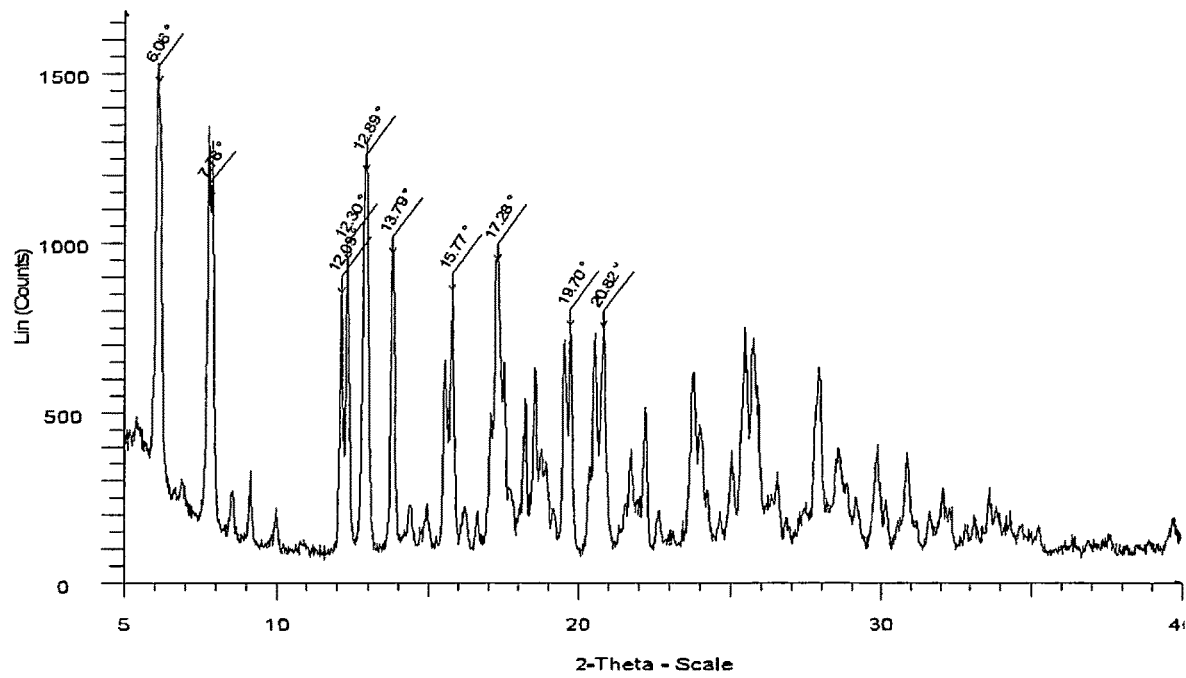
FIG. 11 shows the powder X-ray diffraction pattern of another fenofibric acid salt with berberine (Form G salt).

Form G was analyzed by XRPD. The XRPD pattern of Form G salt is shown in FIG. 11 and the results are tabulated in Table 7.

Table 7. XRPD Peaks for Form G

| Angle (2θ ± 0.2°) | Intensity (%) |
|---|---|
| 6.1 | 100.0 |
| 12.9 | 82.2 |
| 7.8 | 76.7 |
| 13.8 | 65.7 |
| 12.3 | 64.5 |
| 17.3 | 64.4 |
| 15.8 | 58.4 |
| 12.1 | 57.9 |
| 19.7 | 51.2 |
| 20.8 | 51.0 |

Example 8

Preparation of an Exemplary Berberine Salt of Fenofibric Acid (Form H Salt)

20.1 mg of Form A salt of the berberine salt of fenofibric acid was suspended in 1.0 ml of EtOAc to produce a slurry. The slurry was stirred at the ambient condition for 3 days. The solid was filtered, and crystalline Form H salt was obtained.

Figure 12:
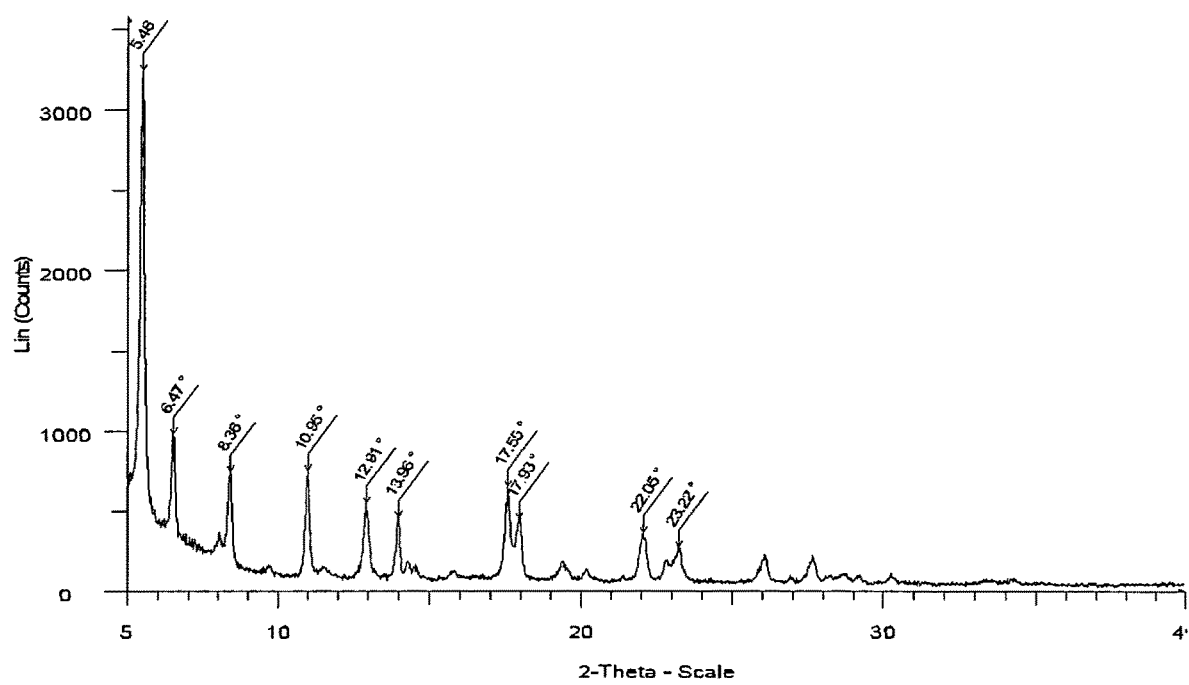
FIG. 12 shows the powder X-ray diffraction pattern of another fenofibric acid salt with berberine (Form H salt).

Form H was analyzed by XRPD. The XRPD pattern of Form G salt is shown in FIG. 12 and the results are tabulated in Table 8.

Table 8. XRPD Peaks for Form G

| Angle (2θ ± 0.2°) | Intensity (%) |
|---|---|
| 5.5 | 100.0 |
| 6.5 | 30.3 |
| 10.9 | 23.1 |
| 8.3 | 23.0 |
| 17.5 | 20.1 |
| 12.9 | 17.0 |
| 14.0 | 14.3 |
| 17.9 | 13.9 |
| 22.0 | 11.3 |
| 8.0 | 11.2 |

While this disclosure may be embodied in many different forms, the described scientific papers and other referenced materials mentioned herein are incorporated by reference in their entirety. Furthermore, the disclosure encompasses any possible combination of some or all the various embodiments mentioned herein, described herein and/or incorporated herein. In addition, the disclosure encompasses any possible combination that also specifically excludes any one or some of the various embodiments mentioned herein, described herein and/or incorporated herein.

The above disclosure is intended to be illustrative and not exhaustive. This description will suggest many variations and alternatives to one of ordinary skill in this art. All these alternatives and variations are intended to be included within the scope of the following claims where the term "comprising" means "including, but not limited to". Those familiar with the art may recognize other equivalents to the specific embodiments described herein which equivalents are also intended to be encompassed by the following claims.

What is claimed is:

1. A fenofibric acid salt with berberine or its analogues comprising neutralized fenofibric acid as an anion and berberine or berberine analog as a cation, wherein the salt has a molar ratio of the neutralized fenofibric acid and berberine or berberine analog of from about 0.9:1 to about 1:0.9; wherein the salt is a crystalline solid of at least about 90% crystalline material; wherein the berberine or berberine analog has one or more of the following structures;

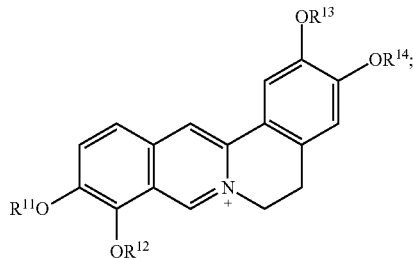

wherein $R^{11}$ and $R^{12}$ are independently H, $CH_3$, or together a —$CH_2$— or substituted —$CH_2$— group; and $R^{13}$ and $R^{14}$ are independently H, $CH_3$, or together a —$CH_2$— or substituted —$CH_2$— group;

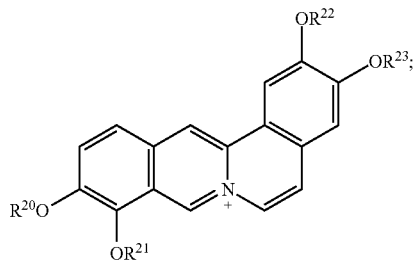

wherein $R^{20}$ and $R^{21}$ are independently H, $CH_3$, or together a —$CH_2$— or substituted —$CH_2$— group; and $R^{22}$ and $R^{23}$ are independently H, $CH_3$, or together a —$CH_2$— or substituted —$CH_2$— group; and

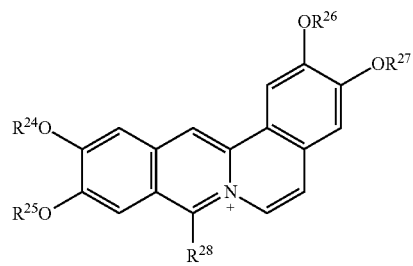

wherein $R^{24}$ and $R^{25}$ are independently H, $CH_3$, or together a —$CH_2$— or substituted —$CH_2$— group; and $R^{26}$ and $R^{27}$ are independently H, $CH_3$, or together a —$CH_2$— or substituted —$CH_2$— group; $R^{28}$ is H, $CH_3$, OH, —$OCH_3$, or —$OCH_2CH_3$.

2. The salt according to claim 1, wherein the salt is an anhydrous, hydrate, solvate, co-crystal, or a mixture thereof.

3. The salt according to claim 1, wherein the cation is berberine.

4. The salt according to claim 1, wherein the cation comprises a mixture of berberine and one of its analogs; or a mixture of berberine and two or more of its analogs.

5. The salt according to claim 1, wherein the cation is one or more of

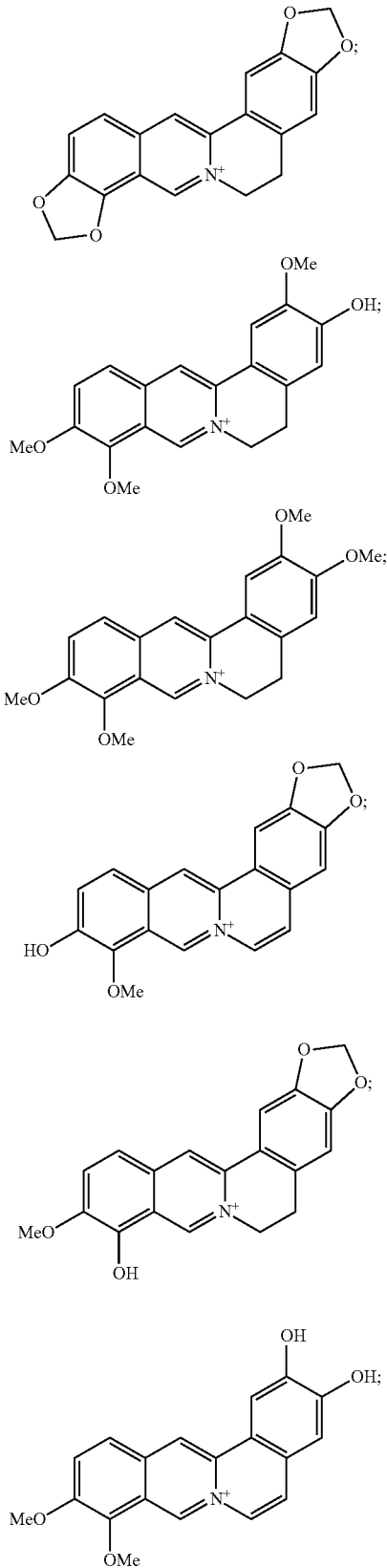

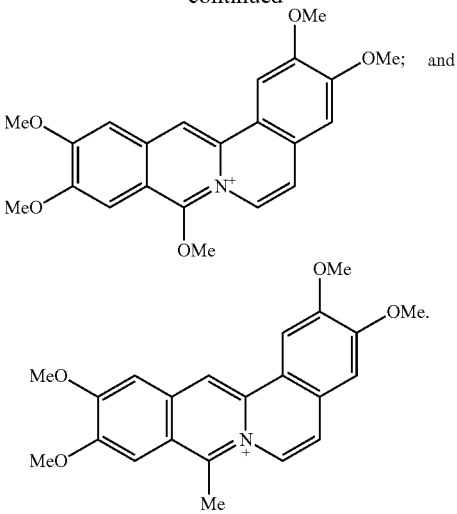

6. The salt according to claim 1, wherein a molar ratio of the neutralize fenofibric acid and berberine or berberine analog is from about 0.95:1 to about 1:0.95.

7. The salt according to claim 1, wherein the salt is a mixture of multiple crystalline forms.

8. The salt according to claim 1, wherein the cation is berberine; and wherein the salt is in crystalline form and is characterized by an XRPD pattern comprising one or more peaks expressed as 2θ±0.2° of about 6.1°, about 7.8°, about 12.2°, about 15.6°, about 17.3°, about 18.3°, about 18.6°, about 19.6°, about 20.4°, and about 25.4°.

9. The salt according to claim 1, wherein the cation is berberine; and wherein the salt is in crystalline form and is characterized by an XRPD pattern comprising one or more peaks expressed as 2θ±0.2° of about 6.2°, about 8.0°, about 12.4°, about 12.9°, about 15.9°, about 17.3°, about 18.7°, about 19.8°, about 20.9°, and about 25.5°.

10. The salt according to claim 1, wherein the cation is berberine; and wherein the salt is in crystalline form and is characterized by an XRPD pattern comprising one or more peaks expressed as 2θ±0.2° of about 5.5°, about 6.9°, about 7.8°, about 9.7°, about 15.7°, about 15.9°, about 17.0°, about 19.2°, about 20.0°, and about 21.3°.

11. The salt according to claim 1, wherein the salt is in single crystalline form.

12. The salt according to claim 1, wherein the cation is berberine; and wherein the salt is in crystalline form and is characterized by an XRPD pattern comprising at least one or more peaks expressed as 2θ±0.2° of about 5.3°, about 5.6°, about 6.6°, about 8.4°, about 14.0°, about 17.6°, about 19.2°, about 23.4°, about 25.1°, and about 25.7°.

13. The salt according to claim 1, wherein the salt is in anhydrous or hydrate crystalline form.

14. The salt according to claim 1, wherein the cation is berberine; and wherein the salt is in crystalline form and is characterized by an XRPD pattern comprising one or more peaks expressed as 2θ±0.2° of about 5.5°, about 6.5°, about 8.0°, about 8.3°, about 10.9°, about 12.9°, about 14.0°, about 17.5°, about 17.9°, about 22.0°, and about 23.2°.

15. The salt according to claim 1, wherein the salt further comprises a solvate, hydrate, cocrystal, or mixture thereof.

16. A composition comprising a salt of claim 1 and a pharmaceutically acceptable carrier.

17. The composition according to claim 16, wherein the carrier is a diluent, adjuvant, excipient, vehicle, or mixture thereof.

18. The composition according to claim 16, wherein the composition is formulated into tablets, gelcaps, capsules, pills, powders, granulates, suspensions, emulsions, solutions, gels, hydrogels, oral gels, pastes, eye drops, ointments, creams, plasters, drenches, delivery devices, suppositories, enemas, injectables, implants, sprays, or aerosols.

19. The composition according to claim 16, wherein the composition is an immediate release composition or extended release composition.

20. A method of therapeutic or prophylactic treatment of a subject against cardiovascular diseases or conditions comprising: administering a therapeutically effective amount of the fenofibric acid salt with berberine or its analog according to claim 1 to a subject in need of cardiovascular diseases or other conditions care.

* * * * *